(12) United States Patent
Kameyama et al.

(10) Patent No.: US 10,995,079 B2
(45) Date of Patent: May 4, 2021

(54) EPOXY COMPOUND, CURABLE COMPOSITION, CURED PRODUCT, METHOD OF PRODUCING EPOXY COMPOUND, AND REACTIVE DILUENT

(71) Applicant: ENEOS CORPORATION, Tokyo (JP)

(72) Inventors: Atsushi Kameyama, Tokyo (JP); Ryuichi Ueno, Tokyo (JP); Hisashi Sone, Tokyo (JP); Hiroaki Suzuki, Tokyo (JP); Shohei Takata, Tokyo (JP); Takashi Seki, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 25 days.

(21) Appl. No.: 16/084,375

(22) PCT Filed: Mar. 13, 2017

(86) PCT No.: PCT/JP2017/010040
§ 371 (c)(1),
(2) Date: Sep. 12, 2018

(87) PCT Pub. No.: WO2017/159637
PCT Pub. Date: Sep. 21, 2017

(65) Prior Publication Data
US 2019/0071409 A1 Mar. 7, 2019

(30) Foreign Application Priority Data

Mar. 14, 2016 (JP) .............................. JP2016-049712
May 30, 2016 (JP) .............................. JP2016-107724
Jun. 16, 2016 (JP) .............................. JP2016-120014
Sep. 27, 2016 (JP) .............................. JP2016-188868
Sep. 27, 2016 (JP) .............................. JP2016-188882

(51) Int. Cl.
| | |
|---|---|
| C07D 303/06 | (2006.01) |
| C07D 301/14 | (2006.01) |
| C08G 59/20 | (2006.01) |
| C08L 63/00 | (2006.01) |
| C07D 303/04 | (2006.01) |
| C08G 65/14 | (2006.01) |
| C08G 65/10 | (2006.01) |
| C07D 301/12 | (2006.01) |

(52) U.S. Cl.
CPC ......... *C07D 303/06* (2013.01); *C07D 301/12* (2013.01); *C07D 301/14* (2013.01); *C07D 303/04* (2013.01); *C08G 59/20* (2013.01); *C08G 65/105* (2013.01); *C08G 65/14* (2013.01); *C08L 63/00* (2013.01)

(58) Field of Classification Search
CPC ............. C07D 303/06; C07D 3030/04; C07D 301/12; C07D 301/14; C08L 63/00; C08G 65/14; C08G 65/105; C08G 59/20; C08G 59/687
See application file for complete search history.

(56) References Cited

U.S. PATENT DOCUMENTS

| | | |
|---|---|---|
| 3,953,534 A | 4/1976 | Sundt |
| 3,968,070 A | 7/1976 | Sundt |
| 3,979,338 A | 9/1976 | Sundt |
| 4,003,935 A | 1/1977 | Sundt |
| 2019/0071409 A1 | 3/2019 | Kameyama et al. |
| 2019/0085003 A1* | 3/2019 | Chino ..................... C08K 3/22 |

FOREIGN PATENT DOCUMENTS

| | | | | |
|---|---|---|---|---|
| DE | 2249376 | * | 4/1973 | ............... A23L 1/26 |
| EP | 0 118 748 | | 9/1984 | |
| EP | 0453275 A1 | * | 4/1991 | ........... C07D 301/03 |
| JP | 48-44245 | | 6/1973 | |

(Continued)

OTHER PUBLICATIONS

International Search Report dated May 30, 2017 in International Application No. PCT/JP2017/010040.
Extended European Search Report dated Aug. 14, 2019 in corresponding European Patent Application No. 17766636.9.
International Preliminary Report on Patentability dated Sep. 27, 2018 in International Application No. PCT/JP2017/010040.

(Continued)

*Primary Examiner* — Jessica M Roswell
(74) *Attorney, Agent, or Firm* — Wenderoth, Lind & Ponack, L.L.P.

(57) ABSTRACT

The present invention discloses a monoepoxy compound represented by the following Formula (1), a curable composition containing the same, a cured product therefrom, a method of producing the monoepoxy compound, and a reactive diluent containing the monoepoxy compound. The monoepoxy compound represented by the Formula (1) is useful in that it is capable of reducing the viscosity of a curable composition containing the monoepoxy compound, while preventing a reduction in the heat resistance of the curable composition as well as a reduction in the weight of the curable composition upon curing.

(1)

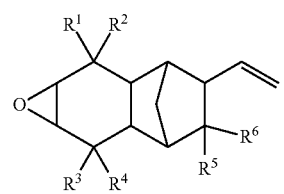

(In the Formula (1), $R^1$ to $R^6$ are each independently selected from the group consisting of a hydrogen atom, an alkyl group, and an alkoxy group.)

17 Claims, 7 Drawing Sheets

(56) References Cited

FOREIGN PATENT DOCUMENTS

| | | | | |
|---|---|---|---|---|
| JP | 49-175 | | 1/1974 | |
| JP | 49-126658 | | 12/1974 | |
| JP | 59-147016 | | 8/1984 | |
| JP | 4-1185 | | 1/1992 | |
| JP | 2015-209464 | | 11/2015 | |
| JP | 2017-165659 | * | 9/2017 | .............. B60C 1/00 |
| JP | 6644659 | | 2/2020 | |
| JP | 6691855 | | 5/2020 | |

OTHER PUBLICATIONS

Office Action dated Oct. 30, 2020 in corresponding Japanese Patent Application No. 2017-102922, with Machine English Translation.
Office Action dated Mar. 2, 2021 in corresponding Japanese Patent Application No. 2017-102922, with English Translation.

* cited by examiner

EPOXY COMPOUND, CURABLE COMPOSITION, CURED PRODUCT, METHOD OF PRODUCING EPOXY COMPOUND, AND REACTIVE DILUENT

CROSS-REFERENCE TO RELATED APPLICATIONS

The present patent application is based upon and claims the benefit of priority from previously filed Japanese Patent Application No. 2016-49712 (filed on Mar. 14, 2016), Japanese Patent Application No. 2016-107724 (filed on May 30, 2016), Japanese Patent Application No. 2016-120014 (filed on Jun. 16, 2016), Japanese Patent Application No. 2016-188868 (filed on Sep. 27, 2016), and Japanese Patent Application No. 2016-188882 (filed on Sep. 27, 2016). The entire disclosures of the above described patent applications are incorporated herein by reference.

FIELD OF THE INVENTION

The present invention relates to an epoxy compound, a curable composition, a cured product, a method of producing an epoxy compound, and a reactive diluent.

BACKGROUND OF THE INVENTION

Representative liquid curable compositions containing epoxy compounds, such as bisphenol A-type epoxy resins, have a high viscosity, and are thus associated with problems in handleability. Incorporation of a solvent into a liquid curable composition has been carried out in order to reduce the viscosity of the curable composition; however, this method has a problem in that the solvent is released during the curing of the curable composition, thereby adversely affecting the environment.

In view of such a problem, techniques have been used to incorporate an epoxy compound or the like, such as butyl glycidyl ether or 1,2-epoxy-4-vinylcyclohexane, as a reactive diluent, into a liquid curable composition.

However, the method of using an epoxy compound as described above is associated with problems such as, for example: the viscosity of the curable composition cannot be sufficiently reduced; the heat resistance of the curable composition may be excessively reduced; and the weight reduction rate of the curable composition upon curing may be increased.

On the other hand, the practical applications of alicyclic epoxy compounds are in progress, as curable compositions having an excellent heat resistance, weather resistance, and the like. Cited Document 1 (JP S49-126658 A) discloses alicyclic diepoxy compounds produced from alicyclic diolefin compounds having a specific naphthalene-type skeleton. However, these alicyclic diepoxy compounds are acicular crystals, which are solids, and thus are not suitable for use in liquid curable compositions.

PRIOR ART DOCUMENT

Patent Document

Patent Document 1: JP S49-126658 A

SUMMARY OF THE INVENTION

Problems to be Solved by the Invention

The present invention has been made in view of the above described problems, and an object of the present invention is to provide a monoepoxy compound capable of reducing the viscosity of a curable composition comprising the monoepoxy compound, while preventing a reduction in the heat resistance of the curable composition as well as a reduction in the weight of the curable composition upon curing.

Further, the present inventors have found out that, by incorporating the monoepoxy compound and a photo-cationic polymerization initiator in combination into a curable composition, it is possible to dramatically improve the adhesion of a cured product obtained by irradiating an active energy ray to the curable composition. The present invention has been made based on the above finding, and it is another object of the present invention to provide a curable composition capable of producing a cured product having an excellent adhesion.

Still further, the present inventors have found out that, by adjusting the ratio of a stereoisomer(s) having a specific structure to equal to or greater than a specific numerical value, in an epoxy compound comprising the specific stereoisomer(s), it is possible to markedly improve the heat resistance of the resulting cured product. The present invention has been made based on the above finding, and it is still another object of the present invention to provide an epoxy compound capable of markedly improving the heat resistance of the resulting cured product.

Means for Solving the Problems

In other words, the present invention encompasses the following inventions.

(1) A monoepoxy compound represented by the following Formula (1):

[Chem. 1]

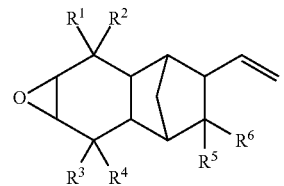

(1)

(wherein $R^1$ to $R^6$ are each independently selected from the group consisting of a hydrogen atom, an alkyl group, and an alkoxy group).

(2) The monoepoxy compound according to (1), comprising a stereoisomer(s) of the compound represented by the Formula (1), wherein the ratio, as measured by $^{13}$C-NMR analysis, of a peak area(s) derived from a stereoisomer(s) in which the bridgehead of the norbornane skeleton and the vinyl group in the Formula (1) are in a trans relationship, to the total peak area within the chemical shift range of from 140 to 145 ppm, is 66% or more.

(3) The monoepoxy compound according to (2), wherein $R^1$ to $R^6$ are all hydrogen atoms, and the stereoisomer(s) in which the bridgehead of the norbornane skeleton and the vinyl group are in a trans relationship is/are represented by any of the following Formulae:

[Chem. 2]

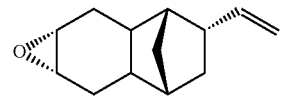

-continued

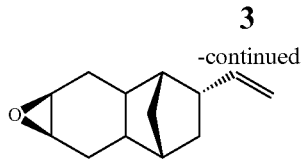

(4) The monoepoxy compound according to (1), wherein, in the $^{13}$C-NMR analysis of the compound represented by the Formula (1), the ratio of the total peak area within the chemical shift range of from 140 to 142 ppm to the total peak area within the chemical shift range of from 140 to 145 ppm is 66% or more.

(5) The monoepoxy compound according to any one of (2) to (4), wherein, in the $^{13}$C-NMR analysis of the compound represented by the Formula (1), the ratio of the area of the first peak from the low magnetic field side, among peaks within the chemical shift range of from 140 to 142 ppm, to the total peak area within the chemical shift range of from 140 to 145 ppm is 35% or more.

(6) A curable composition comprising:

the monoepoxy compound according to any one of (1) to (5); and one kind selected from the group consisting of a curing agent, a thermal cationic polymerization initiator, and a photo-cationic polymerization initiator.

(7) The curable composition according to (6), wherein the curing agent is one or more curing agents selected from the group consisting of phenol compounds, amine compounds, acid anhydride-based compounds, and an amide compounds.

(8) The curable composition according to (6), wherein the thermal cationic polymerization initiator is selected from the group consisting of aromatic sulfonium salt-based thermal cationic polymerization initiators, aromatic iodonium salt-based thermal cationic polymerization initiators, and aluminum complex-based thermal cationic polymerization initiators.

(9) The curable composition according to (6), wherein the photo-cationic polymerization initiator is an aromatic sulfonium salt-based photo-cationic polymerization initiator.

(10) The curable composition according to any one of (6) to (9), further comprising the other epoxy compound different from the monoepoxy compound.

(11) The curable composition according to (10), wherein the other epoxy compound different from the monoepoxy compound is selected from the group consisting of glycidyl ether-type epoxies, glycidyl ester-type epoxies, alicyclic epoxies, and epoxy resins.

(12) The curable composition according to (10) or (11), wherein the content ratio of the monoepoxy compound to the other epoxy compound different from the monoepoxy compound, in the curable composition, is from 1:99 to 75:25 on a mass basis.

(13) A method of producing a cured product, the method comprising the step of curing the curable composition according to any one of (6) to (12).

(14) A cured product from the curable composition according to any one of (6) to (12).

(15) A method of producing the monoepoxy compound according to (1), the method comprising the step of allowing a compound represented by the following Formula (2):

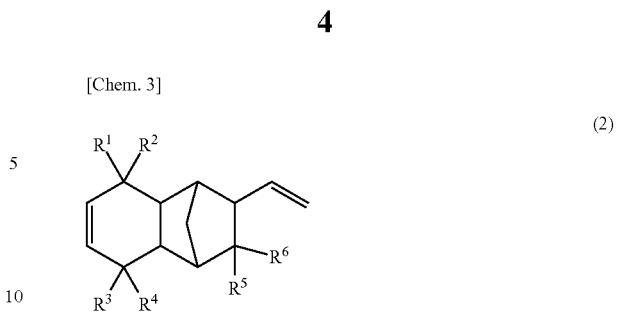

(wherein $R^1$ to $R^6$ are each independently selected from the group consisting of a hydrogen atom, an alkyl group, and an alkoxy group)
to react with a peracid,
wherein the peracid is used in an amount of from 0.10 to 1.80 mol, with respect to 1.00 mol of the compound represented by the Formula (2).

(16) The method according to (15), wherein the peracid is hydrogen peroxide or an organic peracid.

(17) A reactive diluent comprising at least the monoepoxy compound according to (1).

Effect of the Invention

The present invention provides a monoepoxy compound capable of reducing the viscosity of a curable composition comprising the monoepoxy compound, while preventing a reduction in the heat resistance of the curable composition as well as a reduction in the weight of the curable composition upon curing.

Further, the present invention provides a curable composition capable of producing a cured product whose adhesion is dramatically improved.

Still further, the present invention provides a monoepoxy compound which allows for the production of a cured product having a high heat resistance.

DETAILED DESCRIPTION OF THE INVENTION

1. Definition

Figure 1:
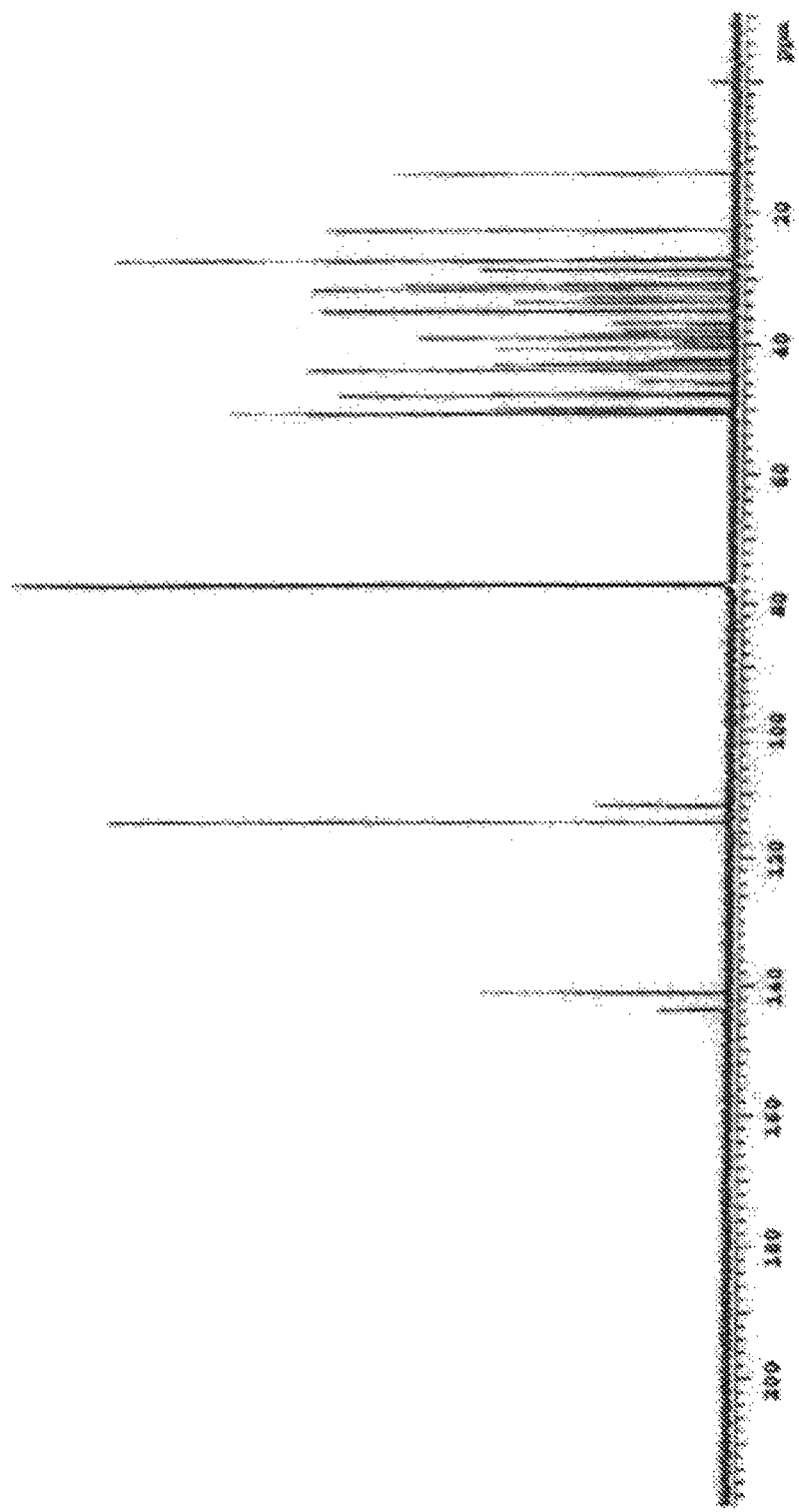
FIG. 1 shows a $^{13}$C-NMR chart of a monoepoxy compound (A) synthesized in Example I 1-1.

In the present specification, the terms "part(s)", "%" and the like used to describe the composition are represented on a mass basis, unless otherwise specified.

In the present specification, the term "epoxy equivalent" is defined by the mass of a monoepoxy compound containing one equivalent of epoxy groups, and can be measured in accordance with JIS K7236.

2. Monoepoxy Compound (1) Monoepoxy Compound

The monoepoxy compound according to the present invention is a monoepoxy compound represented by the following Formula (1):

[Chem. 4]

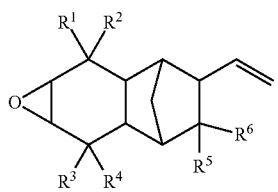

(1)

(wherein $R^1$ to $R^6$ are each independently selected from the group consisting of a hydrogen atom, an alkyl group, and an alkoxy group).

In the above described Formula (1) representing the monoepoxy compound according to the present invention, $R^1$ to $R^6$ are each independently selected from the group consisting of a hydrogen atom, an alkyl group, and an alkoxy group; and the alkyl group preferably has from 1 to 10 carbon atoms, and more preferably from 1 to 5 carbon atoms. Further, the alkyl group may be a linear alkyl group or a branched alkyl group. The alkoxy group preferably has from 1 to 10 carbon atoms, and more preferably from 1 to 5 carbon atoms. It is particularly preferred that $R^1$ to $R^6$ be all hydrogen atoms.

The monoepoxy compound according to the present invention represented by the above described Formula (1) preferably has an epoxy equivalent of from 110 to 1,000 g/eq, more preferably from 150 to 500 g/eq, and still more preferably from 160 to 300 g/eq.

(2) Method of Producing Monoepoxy Compound

The monoepoxy compound according to the present invention, which satisfies the above described Formula (1), can be obtained by a production method comprising the step of allowing a compound represented by the following Formula (2):

[Chem. 5]

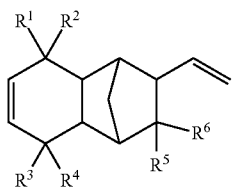

(2)

(wherein $R^1$ to $R^6$ are each independently selected from the group consisting of a hydrogen atom, an alkyl group, and an alkoxy group)
to react with a peracid.

The method of producing the monoepoxy compound according to the present invention is preferably characterized in that, the method comprises the step of allowing the compound represented by the above described Formula (2) to react with a peracid, and the peracid is used in an amount of from 0.10 to 1.80 mol, with respect to 1.00 mol of the compound represented by the above described Formula (2).

In the production of the monoepoxy compound according to the present invention, when the monoepoxy compound obtained by the above described production method has a low purity, the compound is preferably purified by distillation, or by using a column.

Examples of the peracid which can be used in the production of the monoepoxy compound according to the present invention include organic peracids such as performic acid, peracetic acid, perbenzoic acid, and trifluoroperacetic acid; and hydrogen peroxide. Among these, performic acid, peracetic acid and hydrogen peroxide are preferred, since they are industrially available at a low cost, and have a high stability.

It is preferred that the amount used of the peracid in the production of the monoepoxy compound according to the present invention be preferably from 0.10 to 1.80 mol, and more preferably from 0.50 to 1.50 mol, with respect to 1.00 mol of the compound represented by the above described Formula (2).

The compound satisfying the above described Formula (2) can be obtained by the Diels-Alder reaction of 5-vinyl-2-norbornene (VNB) with 1,3-butadiene. VNB can be obtained by the Diels-Alder reaction of 1,3-butadiene with cyclopentadiene.

[Chem. 6]

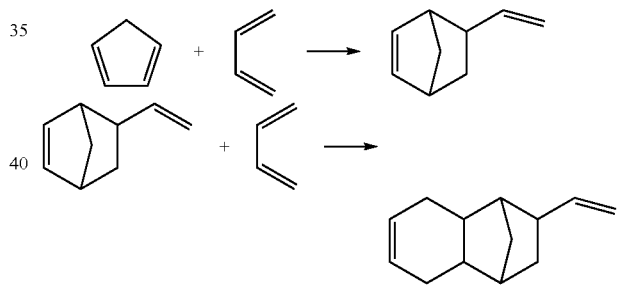

(3) Monoepoxy Compound Comprising Stereoisomer(s)

In cases where $R^1$ to $R^6$ in the monoepoxy compound represented by the above described Formula (1) are all hydrogen atoms, the monoepoxy compound according to the present invention is assumed to include any or all of the stereoisomers as shown below.

[Chem. 7]

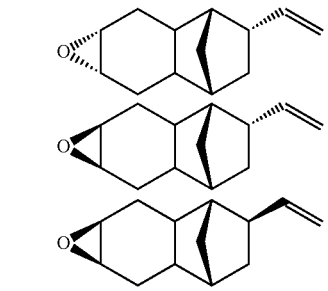

-continued

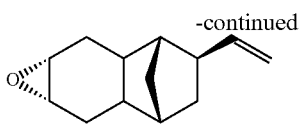

In one embodiment of the monoepoxy compound according to the present invention, the monoepoxy compound is preferably characterized in that the ratio, as measured by $^{13}$C-NMR analysis, of a peak area(s) derived from a stereoisomer(s) in which the bridgehead of the norbornane skeleton and the vinyl group in the Formula (1) are in a trans relationship, to the total peak area within the chemical shift range of from 140 to 145 ppm, is 66% or more. When the monoepoxy compound according to the present invention has the above described characteristics, it is possible to further improve the heat resistance of a cured product obtained by curing a curable composition comprising the monoepoxy compound.

Further, the ratio, as measured by $^{13}$C-NMR analysis, of the peak area(s) derived from the stereoisomer(s) in which the bridgehead of the norbornane skeleton and the vinyl group in the Formula (1) are in a trans relationship, to the total peak area within the chemical shift range of from 140 to 145 ppm, is more preferably 70% or more.

In cases where $R^1$ to $R^6$ in the monoepoxy compound represented by the above described Formula (1) are all hydrogen atoms, examples of the stereoisomer in which the bridgehead of the norbornane skeleton and the vinyl group are in a trans relationship include the following two isomers.

[Chem. 8]

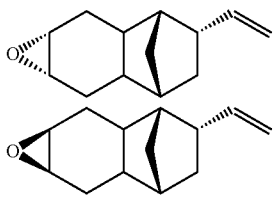

In another embodiment of the monoepoxy compound according to the present invention, it is preferred that the monoepoxy compound be characterized in that, in the $^{13}$C-NMR analysis of the compound represented by the Formula (1), the ratio of the total peak area within the chemical shift range of from 140 to 142 ppm to the total peak area within the chemical shift range of from 140 to 145 ppm is 66% or more.

It is more preferred that the monoepoxy compound be characterized in that, in the $^{13}$C-NMR analysis of the compound represented by the Formula (1), the ratio of the total peak area within the chemical shift range of from 140 to 142 ppm to the total peak area within the chemical shift range of from 140 to 145 ppm is 70% or more.

Further, it is preferred that, in the $^{13}$C-NMR analysis of the compound represented by the Formula (1), the ratio of the area of the first peak from the low magnetic field side, among peaks within the chemical shift range of from 140 to 142 ppm, to the total peak area within the chemical shift range of from 140 to 145 ppm is 35% or more, and more preferably 40% or more.

By subjecting the monoepoxy compound obtainable by the production method described in the above section (2) to a preparative distillation, it is possible to adjust the ratio, as measured by $^{13}$C-NMR analysis, of the peak area(s) derived from the stereoisomer(s) in which the bridgehead of the norbornane skeleton and the vinyl group are in a trans relationship, to the total peak area within the chemical shift range of from 140 to 145 ppm, in the monoepoxy compound represented by the above described Formula (1). Further, by subjecting the monoepoxy compound obtainable by the production method described in the above section (2) to a preparative distillation, it is possible to adjust the ratio of the total peak area within the chemical shift range of from 140 to 142 ppm to the total peak area within the chemical shift range of from 140 to 145 ppm, in the $^{13}$C-NMR analysis of the compound represented by the Formula (1). The method of adjusting the above described ratios is not limited to that described above, and the ratios can also be adjusted, for example, by silica gel chromatography or liquid chromatography.

(4) Utility of Monoepoxy Compound

When the monoepoxy compound according to the present invention is incorporated into a curable composition, it is possible to plasticize, and to reduce the viscosity of, the resulting curable composition, while preventing a reduction in the heat resistance of the curable composition as well as a reduction in the weight of the curable composition upon curing. Accordingly, the monoepoxy compound can be suitably used in the field of: various types of coatings for cans, plastics, papers, wood, and the like; inks; adhesive agents; sealants; electric and electronic materials; carbon fiber reinforced resins; and the like.

More specifically, the monoepoxy compound can be suitably used in: three-dimensional molding materials, acid removers, furniture coatings, decorative coatings, automobile undercoatings, finishing coats, coatings for beverage cans and other types of cans, UV curable inks, protective films for optical disk recording layers, protective films for color filters, adhesive agents for bonding optical disks, adhesive agents for optical materials, die bonding agents for semiconductor devices, sealing materials for organic EL displays, sealing materials for CCDs and light receiving apparatuses such as infrared radiation sensors, sealing materials for light emitting apparatuses such as LEDs and organic ELs, optical semiconductor-related members such as optical circuit boards, optical connectors and lenses, optical waveguides, photoresists, composite glass such as tempered glass and glass for crime prevention, and the like. Further, the monoepoxy compound is also useful as a monomer as a component of a polymer, or as a silane coupling agent precursor.

Further, the monoepoxy compound according to the present invention can be suitably used as a component of a reactive diluent. In the present invention, the reactive diluent refers to an additive which has a high reactivity due to containing a compound having an epoxy group, and which allows the plasticization or the viscosity adjustment (reduction) of a curable composition containing the same.

When the monoepoxy compound represented by the above described Formula (1) and a photo-cationic polymerization initiator are incorporated into a curable composition, it is possible to dramatically improve the adhesion of a cured product obtained by curing the curable composition by an active energy ray. Further, the curable composition according to the present invention has a high heat resistance.

In addition, when a curable composition comprises the monoepoxy compound of a preferred embodiment as described in the description of the above section "(3) Monoepoxy Compound Comprising Stereoisomer(s)", the heat resistance of a cured product obtained by curing the curable composition can further be improved. The content of the monoepoxy compound in the curable composition is preferably from 1 to 90 parts by mass, and more preferably from 5 to 75 parts by mass, with respect to 100 parts by mass of the curable composition. By using the monoepoxy compound and a thermal cationic polymerization initiator in combination, the heat resistance of the resulting cured product can be improved to an even higher level. The above combination also enables to improve the transparency of the resulting cured product.

3. Curable Composition

The curable composition according to the present invention is characterized in that it comprises: the monoepoxy compound represented by the above described Formula (1); and a curing agent, a thermal cationic polymerization initiator or a photo-cationic polymerization initiator. In addition, the curable composition according to the present invention is characterized in that it further comprises the other epoxy compound different from the monoepoxy compound. The curable composition according to the present invention may comprise two or more monoepoxy compounds represented by the above described Formula (1).

When the curable composition according to the present invention comprises the monoepoxy compound represented by the above described Formula (1), the viscosity of the curable composition can be reduced. Further, it is possible to prevent a reduction in the heat resistance of a cured product obtained by curing the curable composition as well as a reduction in the weight which may occur upon curing of the curable composition.

In addition, when the monoepoxy compound represented by the above described Formula (1) and a photo-cationic polymerization initiator are incorporated into the curable composition, it is possible to dramatically improve the adhesion of a cured product obtained by curing the curable composition by an active energy ray. Further, the curable composition according to the present invention has a high heat resistance. Although the curable composition according to the present invention may contain other compounds such as those described later, it is preferred that the content of the monoepoxy compound represented by the above described Formula (1) in the curable composition according to the present invention be preferably from 1 to 90% by mass, and more preferably from 5 to 75% by mass, from the viewpoint of improving the adhesion of the resulting cured product.

In one preferred embodiment of the curable composition according to the present invention, the curable composition comprises: the monoepoxy compound of a preferred embodiment as described in the description of the above section "(3) Monoepoxy Compound Comprising Stereoisomer(s)"; and a curing agent, a thermal cationic polymerization initiator or a photo-cationic polymerization initiator. When the curable composition comprises the above described monoepoxy compound, the heat resistance of a cured product obtained by curing the curable composition can further be improved. The content of the monoepoxy compound in the curable composition is preferably from 1 to 90 parts by mass, and more preferably from 5 to 75 parts by mass, with respect to 100 parts by mass of the curable composition.

(1) Curing Agent

Examples of the curing agent which can be contained in the curable composition according to the present invention include acid anhydride-based curing agents, amine-based curing agents, phenol-based curing agents, and latent curing agents.

Examples of the acid anhydride-based curing agent include hexahydrophthalic anhydride, methylhexahydrophthalic anhydride, tetrahydrophthalic anhydride, methyltetrahydrophthalic anhydride, endomethylenetetrahydrophthalic anhydride, methylnadic anhydride, methylbutenyltetrahydrophthalic anhydride, hydrogenated methylnadic anhydride, trialkyltetrahydrophthalic anhydride, cyclohexanetricarboxylic anhydride, methylcyclohexenedicarboxylic anhydride, methylcyclohexanetetracarboxylic acid dianhydride, maleic anhydride, phthalic anhydride, succinic anhydride, dodecenylsuccinic anhydride, octenylsuccinic anhydride, pyromellitic anhydride, trimellitic anhydride, alkylstyrene-maleic anhydride copolymer, chlorendic anhydride, polyazelaic anhydride, benzophenone tetracarboxylic anhydride, ethylene glycol bisanhydrotrimellitate, glycerol tristrimellitate, glycerin bis(anhydrotrimellitate) monoacetate, benzophenonetetracarboxylic acid, polyadipic anhydride, polysebacic anhydride, poly(ethyloctadecanedioic acid) anhydride, poly(phenylhexadecanedioic acid) anhydride, HET anhydride, and norbornane-2,3-dicarboxylic anhydride.

Examples of the amine-based curing agent include polyoxyethylene diamine, polyoxypropylene diamine, polyoxybutylene diamine, polyoxypentylene diamine, polyoxyethylene triamine, polyoxypropylene triamine, polyoxybutylene triamine, polyoxypentylene triamine, diethylene triamine, triethylene tetramine, tetraethylene pentamine, m-xylene diamine, trimethylhexamethylene diamine, 2-methylpentamethylene diamine, diethylaminopropylamine, isophorone diamine, 1,3-bisaminomethylcyclohexane, bis(4-aminocyclohexyl)methane, norbornane diamine, 1,2-diaminocyclohexane, diaminodiphenylmethane, metaphenylene diamine, diaminodiphenyl sulfone, and N-aminoethylpiperazine.

Examples of the phenol-based curing agent include xylylene skeleton-containing phenol novolac resins, dicyclopentadiene skeleton-containing phenol novolac resins, biphenyl skeleton-containing phenol novolac resins, fluorene skeleton-containing phenol novolac resins, terpene skeleton-containing phenol novolac resins, bisphenol A novolac, bisphenol F novolac, bisphenol S novolac, bisphenol AP novolac, bisphenol C novolac, bisphenol E novolac, bisphenol Z novolac, biphenol novolac, tetramethyl bisphenol A novolac, dimethyl bisphenol A novolac, tetramethyl bisphenol F novolac, dimethyl bisphenol F novolac, tetramethyl bisphenol S novolac, dimethyl bisphenol S novolac, tetramethyl-4,4'-biphenol novolac, trishydroxyphenylmethane novolac, resorcinol novolac, hydroquinone novolac, pyrogallol novolac, diisopropylidene novolac, 1,1-di-4-hydroxyphenylfluorene novolac, phenolated polybutadiene novolac, phenol novolac, cresol novolac, ethylphenol novolac, butylphenol novolac, octylphenol novolac, and naphthol novolac.

Examples of the latent curing agent include dicyandiamide, adipic acid dihydrazide, sebacic acid dihydrazide, dodecanedioic acid dihydrazide, isophthalic acid dihydrazide, ketimines, imidazole compounds, dihydrazide compounds, amine adduct-based latent curing agents. The curable composition according to the present invention may contain one kind, or two or more kinds of the curing agents as described above.

In a preferred embodiment of the curable composition according to the present invention, the curing agent is one or more curing agents selected from the group consisting of acid anhydride-based curing agents, amine-based curing agents, phenol-based curing agents and latent curing agents.

The content of the curing agent in the curable composition according to the present invention is preferably selected as appropriate depending on the type of the curing agent used. In cases where an acid anhydride-based curing agent, an amine-based curing agent, or a phenol-based curing agent is used as the curing agent, for example, the content of the curing agent is preferably from 0.5 to 1.5 equivalent, and more preferably from 0.8 to 1.2 equivalent, with respect to one equivalent of epoxy groups in the entire curable composition. In cases where a latent curing agent is used as the curing agent, for example, the content of the curing agent is preferably from 1 to 30 parts by mass, and more preferably from 5 to 20 parts by mass, with respect to 100 parts by mass of the curable composition.

(2) Curing Accelerator

The curable composition according to the present invention may further contain a curing accelerator. Examples of the curing accelerator include: phosphines and quaternary salts thereof, such as triphenylphosphine, triphenylbenzylphosphonium tetraphenylborate, tetrabutylphosphonium diethylphosphorodithioate, tetraphenylphosphonium bromide, tetrabutylphosphonium acetate, tetra-n-butylphosphonium bromide, tetra-n-butylphosphonium benzotriazolate, tetra-n-butylphosphonium tetrafluoroborate, tetra-n-butylphosphonium tetraphenylborate, methyltriphenylphosphonium bromide, ethyltriphenylphosphonium bromide, ethyltriphenylphosphonium iodide, ethyltriphenylphosphonium acetate, methyltri-n-butylphosphonium dimethylphosphate, n-butyltriphenylphosphonium bromide, benzyltriphenylphosphonium chloride, and tetraphenylphosphonium tetraphenylborate; imidazoles such as 2-ethyl-4-methylimidazole, 1,2-dimethylimidazole, 1-benzyl-2-phenylimidazole, 2-methylimidazole, 2-phenylimidazole, 1-(2-cyanoethyl)-2-ethyl-4-methylimidazole, 2,4-diamino-6-[2-methylimidazolyl-(1)]ethyl-s-triazine, 2-phenylimidazoline, and 2,3-dihydro-1H-pyrrolo[1,2-a]benzimidazole; tertiary amines and quaternary salts thereof such as, tris(dimethylaminomethyl)phenol, benzyldimethylamine, and tetrabutylammonium bromide; super strong basic organic compounds such as 1,8-diazabicyclo(5,4,0)undecene-7 and 1,5-diazabicyclo(4,3,0)nonene-5; organic metal carboxylates such as zinc octylate, zinc laurate, zinc stearate, and tin octylate; metal-organic chelate compounds such as benzoylacetone zinc chelate, dibenzoylmethane zinc chelate and ethyl acetoacetate zinc chelate; and tetra-n-butylsulfonium-o,o-diethyl phosphorodithionate. The curable composition according to the present invention may contain one kind, or two or more kinds of the curing accelerators as described above.

The content of the curing accelerator in the curable composition according to the present invention is preferably from 0.1 to 6 parts by mass with respect to 100 parts by mass of the total amount of the curable composition.

(3) Thermal Cationic Polymerization Initiator

Examples of the thermal cationic polymerization initiator which can be contained in the curable composition according to the present invention include thermal cationic polymerization initiators such as: onium salts composed of at least one cation selected from an aromatic sulfonium, an aromatic iodonium, an aromatic diazonium, pyridinium and the like, and at least one anion selected from $BF_4^-$, $PF_6^-$, $SbF_6^-$, $AsF_6^-$, $CF_3SO_3^-$, $(CF_3SO_2)_2N^-$ and $B(C_6F_5)_4^-$; and aluminum complexes.

Examples of aromatic sulfonium salt-based thermal cationic polymerization initiators include: hexafluoroantimonate salts such as (2-ethoxy-1-methyl-2-oxoethyl)methyl-2-naphthalenylsulfonium hexafluoroantimonate, 4-(methoxycarbonyloxy)phenylbenzylmethylsulfonium hexafluoroantimonate, 4-acetoxyphenyldimethylsulfonium hexafluoroantimonate, 4-hydroxyphenylbenzylmethylsulfonium hexafluoroantimonate, 4-hydroxyphenyl(o-methylbenzyl)methylsulfonium hexafluoroantimonate, 4-hydroxyphenyl(α-naphthylmethyl)methylsulfonium hexafluoroantimonate, diphenyl-4-(phenylthio)phenylsulfonium hexafluoroantimonate, triphenylsulfonium hexafluoroantimonate, bis[4-(di(4-(2-hydroxyethoxy))phenylsulfonio)phenyl]sulfide bishexafluoroantimonate, and bis[4-(diphenylsulfonio)phenyl]sulfide bishexafluoroantimonate; hexafluorophosphate salts such as (2-ethoxy-1-methyl-2-oxoethyl)methyl-2-naphthalenylsulfonium hexafluorophosphate, 4-acetoxyphenylbenzylmethylsulfonium hexafluorophosphate, 4-hydroxyphenyl(o-methylbenzyl)methylsulfonium hexafluorophosphate, 4-hydroxyphenyl(α-naphthylmethyl)methylsulfonium hexafluorophosphate, diphenyl-4-(phenylthio)phenylsulfonium hexafluorophosphate, triphenylsulfonium hexafluorophosphate, bis[4-(di(4-(2-hydroxyethoxy))phenylsulfonio)phenyl]sulfide bishexafluorophosphate, and bis[4-(diphenylsulfonio)phenyl]sulfide bishexafluorophosphate; hexafluoroarsenate salts such as 4-hydroxyphenyl(o-methylbenzyl)methylsulfonium hexafluoroarsenate, and 4-hydroxyphenylbenzylmethylsulfonium hexafluoroarsenate; tetrafluoroborate salts such as (2-ethoxy-1-methyl-2-oxoethyl)methyl-2-naphthalenylsulfonium tetrafluoroborate, 4-hydroxyphenyl(o-methylbenzyl)methylsulfonium tetrafluoroborate, 4-hydroxyphenylbenzylmethylsulfonium tetrafluoroborate, diphenyl-4-(phenylthio)phenylsulfonium tetrafluoroborate, triphenylsulfonium tetrafluoroborate, bis[4-(di(4-(2-hydroxyethoxy))phenylsulfonio)phenyl]sulfide bistetrafluoroborate, and bis[4-(diphenylsulfonio)phenyl]sulfide bistetrafluoroborate; trifluoromethanesulfonate salts such as 4-hydroxyphenyl(o-methylbenzyl)methylsulfonium trifluoromethanesulfonate, and 4-hydroxyphenylbenzylmethylsulfonium trifluoromethanesulfonate; trifluoromethanesulfonate salts such as diphenyl-4-(phenylthio)phenylsulfonium trifluoromethanesulfonate; bis(trifluoromethanesulfone)imide salts such as 4-hydroxyphenyl(α-naphthylmethyl)methylsulfonium bis(trifluoromethanesulfone)imide, and 4-hydroxyphenylbenzylmethylsulfonium bis(trifluoromethanesulfone)imide; tetrakis(pentafluorophenyl)borate salts such as (2-ethoxy-1-methyl-2-oxoethyl)methyl-2-naphthalenylsulfonium tetrakis(pentafluorophenyl)borate, 4-(methoxycarbonyloxy)phenylbenzylmethylsulfonium tetrakis(pentafluorophenyl)borate, 4-hydroxyphenyl(o-methylbenzyl)methylsulfonium tetrakis(pentafluorophenyl)borate, 4-hydroxyphenyl(α-naphthylmethyl)methylsulfonium tetrakis(pentafluorophenyl)borate, 4-hydroxyphenylbenzylmethylsulfonium tetrakis(pentafluorophenyl)borate, diphenyl-4-(phenylthio)phenylsulfonium tetrakis(pentafluorophenyl)borate, triphenylsulfonium tetrakis(pentafluorophenyl)borate, bis[4-(di(4-(2-hydroxyethoxy))phenylsulfonio)phenyl]sulfide tetrakis(pentafluorophenyl)borate, and bis[4-(diphenylsulfonio)phenyl]sulfide tetrakis(pentafluorophenyl)borate.

Specific examples of aromatic iodonium salt-based thermal cationic polymerization initiators include phenyliodonium hexafluorophosphate, diphenyliodonium hexafluoroantimonate, diphenyliodonium tetrafluoroborate, diphenyliodonium tetrakis(pentafluorophenyl)borate, diphenyliodonium hexafluorophosphate, diphenyliodonium trifluoromethanesulfonate, bis(dodecylphenyl)iodonium hexafluorophosphate, bis(dodecylphenyl)iodonium hexafluoroantimonate, bis(dodecylphenyl)iodonium tetrafluoroborate, bis(dodecylphenyl)iodonium tetrakis(pentafluorophenyl)borate, 4-methylphenyl-4-(1-methylethyl)phenyliodonium hexafluorophosphate, 4-methylphenyl-4-(1-methylethyl)phenyliodonium hexafluoroantimonate, 4-methylphenyl-4-(1-methylethyl)phenyliodonium tetrafluoroborate, and 4-methylphenyl-4-(1-methylethyl)phenyliodonium tetrakis(pentafluorophenyl)borate.

Specific examples of aromatic diazonium salt-based thermal cationic polymerization initiators include phenyldiazonium hexafluorophosphate, phenyldiazonium hexafluoroantimonate, phenyldiazonium tetrafluoroborate and phenyldiazonium tetrakis(pentafluorophenyl)borate.

Specific examples of pyridinium salt-based thermal cationic polymerization initiators include 1-benzyl-2-cyanopyridinium hexafluorophosphate, 1-benzyl-2-cyanopyridinium hexafluoroantimonate, 1-benzyl-2-cyanopyridinium tetrafluoroborate, 1-benzyl-2-cyanopyridinium tetrakis(pentafluorophenyl)borate, 1-(naphthylmethyl)-2-cyanopyridinium hexafluorophosphate, 1-(naphthylmethyl)-2-cyanopyridinium hexafluoroantimonate, 1-(naphthylmethyl)-2-cyanopyridinium tetrafluoroborate, and 1-(naphthylmethyl)-2-cyanopyridinium tetrakis(pentafluorophenyl)borate.

Examples of aluminum complex-based thermal cationic polymerization initiators include aluminum carboxylates; aluminum alkoxides, aluminium chlorides, aluminum (alkoxide) acetoacetic acid chelate, acetoacetonato aluminum, and ethylacetoacetato aluminum.

Examples of phosphonium salt-based thermal cationic polymerization initiators include ethyltriphenylphosphonium hexafluoroantimonate, and tetrabutylphosphonium hexafluoroantimonate.

Examples of quaternary ammonium salt-based thermal cationic polymerization initiators include N,N-dimethyl-N-benzylanilinium hexafluoroantimonate, N,N-diethyl-N-benzylanilinium tetrafluoroborate, N,N-dimethyl-N-benzylpyridinium hexafluoroantimonate, N,N-diethyl-N-benzylpyridinium trifluoromethanesulfonic acid, N,N-dimethyl-N-(4-methoxybenzyl)pyridinium hexafluoroantimonate, N,N-diethyl-N-(4-methoxybenzyl)pyridinium hexafluoroantimonate, N,N-diethyl-N-(4-methoxybenzyl)toluidinium hexafluoroantimonate, and N,N-dimethyl-N-(4-methoxybenzyl)toluidinium hexafluoroantimonate.

The curable composition according to the present invention may contain one kind, or two or more kinds of the thermal cationic polymerization initiators as described above.

In a more preferred embodiment of the curable composition according to the present invention, the thermal cationic polymerization initiator to be contained in the curable composition is characterized in that it is selected from the group consisting of aromatic sulfonium salt-based thermal cationic polymerization initiators, aromatic iodonium salt-based thermal cationic polymerization initiators, and aluminum complex-based thermal cationic polymerization initiators.

The content of the thermal cationic polymerization initiator in the curable composition according to the present invention is preferably selected as appropriate depending on the type of the thermal cationic polymerization initiator used. For example, in the case of using the thermal cationic polymerization initiator, the content thereof is preferably from 0.1 to 15 parts by mass, and more preferably from 0.3 to 7 parts by mass, with respect to 100 parts by mass of the curable composition.

(4) Photo-Cationic Polymerization Initiator

The photo-cationic polymerization initiator to be contained in the curable composition according to the present invention is one which generates cationic species or Lewis acid when irradiated with an active energy ray such as a visible ray, UV light, an X ray or an electron beam, thereby initiating a polymerization reaction of a cationically polymerizable compound. As the photo-cationic polymerization initiator to be contained in the curable composition according to the present invention, it is possible to use, for example, a compound such as an onium salt, a metallocene complex, or an iron-allene complex. Examples of the onium salt which can be used include aromatic sulfonium salts, aromatic iodonium salts, aromatic diazonium salts, aromatic phosphonium salts and aromatic selenium salts. As the counter ions for these salts, anions such as $CF_3SO_3^-$, $BF_4^-$, $PF_6^-$, $AsF_6^-$, and $SbF_6^-$ are used. Among these, it is more preferred to use an aromatic sulfonium salt-based photo-cationic polymerization initiator, since it exhibits an excellent curing performance due to having UV absorption properties even in the wavelength range of 300 nm or more, and allows for providing a cured product having a good mechanical strength and adhesion strength. The curable composition according to the present invention may contain two or more kinds of the photo-cationic polymerization initiators.

Examples of the aromatic sulfonium salt include diphenyl-4-(phenylthio)phenylsulfonium hexafluorophosphate, 4,4'-bis(diphenylsulfonio)diphenylsulfide bishexafluorophosphate, 4,4'-bis[di(β-hydroxyethoxy)phenylsulfonio]diphenylsulfide bishexafluoroantimonate, 4,4'-bis[di(β-hydroxyethoxy)phenylsulfonio]diphenylsulfide bishexafluorophosphate, 7-[di(p-toluyl)sulfonio]-2-isopropylthioxanthone hexafluoroantimonate, 7-[di(p-toluyl)sulfonio]-2-isopropylthioxanthone tetrakis(pentafluorophenyl)borate, 4-phenylcarbonyl-4'-diphenylsulfonio-diphenylsulfide hexafluorophosphate, 4-(p-tert-butylphenylcarbonyl)-4'-diphenylsulfonio-diphenylsulfide hexafluoroantimonate, 4-(p-tert-butylphenylcarbonyl)-4'-di(p-toluyl)sulfonio-diphenylsulfide tetrakis(pentafluorophenyl)borate, diphenyl-4-(phenylthio)phenylsulfonium hexafluoroantimonate, triphenylsulfonium trifluoromethanesulfonate, bis[4-(diphenylsulfonio)phenyl]sulfide bishexafluoroantimonate, and (4-methoxyphenyl)diphenylsulfonium hexafluoroantimonate.

Examples of the aromatic iodonium salt include diphenyliodonium tetrakis(pentafluorophenyl)borate, diphenyliodonium hexafluorophosphate, diphenyliodonium hexafluoroantimonate, di(4-nonylphenyl)iodonium hexafluorophosphate, (4-methoxyphenyl)phenyliodonium hexafluoroantimonate, and bis(4-t-butylphenyl)iodonium hexafluorophosphate.

Examples of the aromatic diazonium salt include benzenediazonium hexafluoroantimonate, benzenediazonium hexafluorophosphate, benzenediazonium tetrafluoroborate, and 4-chlorobenzenediazonium hexafluorophosphate.

Examples of the aromatic phosphonium salt include benzyltriphenylphosphonium hexafluoroantimonate.

Examples of the aromatic selenium salt include triphenylselenium hexafluorophosphate.

Examples of the iron-allene complex include xylene-cyclopentadienyl iron (II) hexafluoroantimonate, cumene-cyclopentadienyl iron (II) hexafluorophosphate, and xylene-cyclopentadienyl iron (II) tris(trifluoromethylsulfonyl)methanaide.

The content of the photo-cationic polymerization initiator in the curable composition according to the present invention is preferably from 0.1 to 20 parts by mass, and more preferably from 0.3 to 15 parts by mass, with respect to 100 parts by mass of the monoepoxy compound contained in the curable composition, or alternatively, in cases where the curable composition contains the other epoxy compound different from the monoepoxy compound to be described later, an oxetane compound and/or a vinyl ether compound to be described later, with respect to 100 parts by mass of the total amount thereof. When the content of the photo-cationic polymerization initiator is adjusted within the above described numerical range, the heat resistance of the resulting cured product can be improved to an even higher level. In addition, the transparency of the cured product can further be improved.

(5) The Other Epoxy Compound Different from the Monoepoxy Compound

The other epoxy compound different from the monoepoxy compound to be contained in the curable composition according to the present invention is not particularly limited, as long as it is a compound which is other than the monoepoxy compound represented by the above described Formula (1), and which contains one or more epoxy groups, preferably two or more epoxy groups, in the molecule.

Examples of the other epoxy compound to be contained in the curable composition according to the present invention include glycidyl ether-type epoxides, glycidyl ester-type epoxides, glycidyl amine-type epoxides and alicyclic epoxides. The other epoxy compound may be an epoxy resin obtained by polymerizing any of the glycidyl ether-type epoxides, glycidyl ester-type epoxides, glycidyl amine-type epoxides and alicyclic epoxides.

Examples of the glycidyl ether-type epoxide include: glycidyl ethers of divalent phenols such as bisphenol A diglycidyl ether, bisphenol F diglycidyl ether, bisphenol S diglycidyl ether, tetramethyl biphenol diglycidyl ether, hydrogenated bisphenol A diglycidyl ether, and brominated bisphenol A diglycidyl ether; glycidyl ethers of polyvalent phenols such as dihydroxynaphthyl cresol triglycidyl ether, tris(hydroxyphenyl)methane triglycidyl ether, tetrakis(hydroxyphenyl)ethane tetraglycidyl ether, dinaphthyltriol triglycidyl ether, phenol novolac glycidyl ether, cresol novolac glycidyl ether, xylylene skeleton-containing phenol novolac glycidyl ethers, dicyclopentadiene skeleton-containing phenol novolac glycidyl ethers, biphenyl skeleton-containing phenol novolac glycidyl ethers, terpene skeleton-containing phenol novolac glycidyl ethers, bisphenol A novolac glycidyl ether, bisphenol F novolac glycidyl ether, bisphenol S novolac glycidyl ether, bisphenol AP novolac glycidyl ether, bisphenol C novolac glycidyl ether, bisphenol E novolac glycidyl ether, bisphenol Z novolac glycidyl ether, biphenol novolac glycidyl ether, tetramethyl bisphenol A novolac glycidyl ether, dimethyl bisphenol A novolac glycidyl ether, tetramethyl bisphenol F novolac glycidyl ether, dimethyl bisphenol F novolac glycidyl ether, tetramethyl bisphenol S novolac glycidyl ether, dimethyl bisphenol S novolac glycidyl ether, tetramethyl-4,4'-biphenol novolac glycidyl ether, trishydroxyphenylmethane novolac glycidyl ether, resorcinol novolac glycidyl ether, hydroquinone novolac glycidyl ether, pyrogallol novolac glycidyl ether, diisopropylidene novolac glycidyl ether, 1,1-di-4-hydroxyphenylfluorene novolac glycidyl ether, phenolated polybutadiene novolac glycidyl ether, ethylphenol novolac glycidyl ether, butylphenol novolac glycidyl ether, octylphenol novolac glycidyl ether, naphthol novolac glycidyl ether, and hydrogenated phenol novolac glycidyl ether; glycidyl ethers of divalent alcohols such as ethylene glycol diglycidyl ether, propylene glycol diglycidyl ether, tetramethylene glycol diglycidyl ether, 1,6-hexanediol diglycidyl ether, cyclohexanedimethylol diglycidyl ether, polyethylene glycol diglycidyl ether, and polypropylene glycol diglycidyl ether; glycidyl ethers of polyols such as trimethylolpropane triglycidyl ether, glycerin triglycidyl ether, pentaerythritol tetraglycidyl ether, sorbitol hexaglycidyl ether, and polyglycerin polyglycidyl ether; and triglycidyl isocyanurate.

Examples of the glycidyl ester-type epoxide include: glycidyl esters of carboxylic acids such as glycidyl methacrylate, phthalic acid diglycidyl ester, isophthalic acid diglycidyl ester, terephthalic acid diglycidyl ester, cyclohexanedicarboxylic acid diglycidyl ester, and trimellitic acid triglycidyl ester; and glycidyl ester-type polyepoxides.

Examples of the glycidyl amine-type epoxide include: glycidyl aromatic amines such as N,N-diglycidylaniline, N,N-diglycidyltoluidine, N,N,N',N'-tetraglycidyldiaminodiphenylmethane, N,N,N',N'-tetraglycidyldiaminodiphenylsulfone, and N,N,N',N'-tetraglycidyldiethyldiphenylmethane; and glycidyl heterocyclic amines such as bis(N,N-diglycidylaminocyclohexyl)methane (hydride of N,N,N',N'-tetraglycidyldiaminodiphenylmethane), N,N,N',N'-tetraglycidyl-1,3-(bisaminomethyl)cyclohexane (hydride of N,N,N',N'-tetraglycidylxylylene diamine), trisglycidylmelamine, triglycidyl-p-aminophenol, N-glycidyl-4-glycidyloxypyrrolidone.

Examples of the alicyclic epoxide include vinyl cyclohexene dioxide, limonene dioxide, dicyclopentadiene dioxide, bis(2,3-epoxycyclopentyl) ether, ethylene glycol bisepoxy dicyclopentyl ether, 3,4-epoxy-6-methylcyclohexylmethyl 3',4'-epoxy-6'-methylcyclohexane carboxylate, 3,4-epoxycyclohexylmethyl 3,4-epoxycyclohexane carboxylate, 3,4-epoxy-1-methylcyclohexyl 3,4-epoxy-1-methylhexane carboxylate, 3,4-epoxy-3-methylcyclohexylmethyl 3,4-epoxy-3-methylhexane carboxylate, 3,4-epoxy-5-methylcyclohexylmethyl 3,4-epoxy-5-methylcyclohexane carboxylate, 2-(3,4-epoxycyclohexyl-5,5-spiro-3,4-epoxy)cyclohexane-metadioxane, methylenebis(3,4-epoxycyclohexane), (3,3',4,4'-diepoxy)bicyclohexyl, 1,2-epoxy-(2-oxiranyl)cyclohexane adduct of 2,2-bis(hydroxymethyl)-1-butanol, and tetrahydroindene diepoxide. The curable composition according to the present invention may contain one kind, or two or more kinds of the other epoxy compounds as described above.

From the viewpoint of improving the heat resistance of the resulting cured product, the content of the other epoxy compound described above is preferably from 1 to 99% by mass, and more preferably from 5 to 95% by mass, with respect to the amount of the curable composition according to the present invention.

In the curable composition according to the present invention, the content ratio of the monoepoxy compound to the other epoxy compound different from the monoepoxy compound is preferably from 1:99 to 75:25, and more preferably from 5:95 to 50:50, on a mass basis.

In a preferred embodiment of the curable composition according to the present invention, the other epoxy compound different from the monoepoxy compound is an epoxy resin.

In a more preferred embodiment of the curable composition according to the present invention, the other epoxy compound different from the monoepoxy compound, to be contained in the curable composition, is characterized in that it is selected from the group consisting of glycidyl ether-type epoxides, glycidyl ester-type epoxides, and alicyclic epoxides.

(6) Reactive Diluent

The curable composition according to the present invention may further contain a reactive diluent, in order to reduce the viscosity thereof. Examples of the reactive diluent include a monoepoxy compound (A) prepared according to the method described in Example I 1, butyl glycidyl ether, 2-ethylhexyl glycidyl ether, glycidyl ether of a mixture of C12 and C13 alcohols, and 1,2-epoxy-4-vinylcyclohexane. The curable composition may contain one kind, or two or more kinds of the reactive diluents as described above. The mixing ratio of the reactive diluent may be selected as appropriate such that the curable composition containing the reactive diluent has a desired viscosity.

(7) Oxetane Compound

The curable composition according to the present invention may further contain an oxetane compound. Examples of the oxetane compound include 1,4-bis[(3-ethyl-3-oxetanylmethoxy)methyl]benzene, 3-ethyl-3-hydroxymethyloxetane, 3-ethyl-3-(phenoxymethyl)oxetane, di[(3-ethyl-3-oxetanyl)methyl] ether, 3-ethyl-3-(2-ethylhexyloxymethyl)oxetane, 3-ethyl-3-(cyclohexyloxymethyl)oxetane, phenol novolac oxetane, 1,3-bis[(3-ethyloxetan-3-yl)]methoxybenzene, oxetanyl silsesquioxane, oxetanyl silicate, bis[1-ethyl (3-oxetanyl)]methyl ether, 4,4'-bis[(3-ethyl-3-oxetanyl) methoxymethyl]biphenyl, 4,4'-bis(3-ethyl-3-oxetanylmethoxy)biphenyl, ethylene glycol (3-ethyl-3-oxetanylmethyl) ether, diethylene glycol bis(3-ethyl-3-oxetanylmethyl) ether, bis(3-ethyl-3-oxetanylmethyl) diphenoate, trimethylolpropane propane tris(3-ethyl-3-oxetanylmethyl) ether, pentaerythritol tetrakis(3-ethyl-3-oxetanylmethyl) ether, and phenol novolac-type oxetane compounds. The curable composition according to the present invention may contain one kind, or two or more kinds of the oxetane compounds as described above.

From the viewpoint of improving the heat resistance of the resulting cured product, the content of the oxetane compound in the curable composition is preferably from 1 to 90% by mass, and more preferably from 5 to 85% by mass.

(8) Vinyl Ether Compound

The curable composition according to the present invention may further contain a vinyl ether compound. Examples of the vinyl ether compound include: monofunctional vinyl ethers such as methyl vinyl ether, ethyl vinyl ether, propyl vinyl ether, and butyl vinyl ether; polyfunctional vinyl ethers such as ethylene glycol divinyl ether, butanediol divinyl ether, cyclohexanedimethanol divinyl ether, cyclohexanediol divinyl ether, trimethylolpropane trivinyl ether, pentaerythritol tetravinyl ether, glycerol trivinyl ether, triethylene glycol divinyl ether, and diethylene glycol divinyl ether; vinyl ether compounds containing a hydroxyl group such as hydroxyethyl vinyl ether, hydroxybutyl vinyl ether, cyclohexanedimethanol monovinyl ether, cyclohexanediol monovinyl ether, 9-hydroxynonyl vinyl ether, propylene glycol monovinyl ether, neopentyl glycol monovinyl ether, glycerol divinyl ether, glycerol monovinyl ether, trimethylolpropane divinyl ether, trimethylolpropane monovinyl ether, pentaerythritol monovinyl ether, pentaerythritol divinyl ether, pentaerythritol trivinyl ether, diethylene glycol monovinyl ether, triethylene glycol monovinyl ether, tetraethylene glycol monovinyl ether, tricyclodecanediol monovinyl ether, and tricyclodecane dimethanol monovinyl ether; and vinyl ethers containing different types of functional groups, such as 2-(2-vinyloxyethoxy)ethyl acrylate, and 2-(2-vinyloxyethoxy)ethyl methacrylate. The curable composition according to the present invention may contain one kind, or two or more kinds of the vinyl ether compounds as described above.

From the viewpoint of improving the heat resistance of the resulting cured product, the content of the vinyl ether compound in the curable composition is preferably from 1 to 90% by mass, and more preferably from 5 to 85% by mass.

(9) Compound Containing Hydroxyl Group

The curable composition according to the present invention may further contain a compound containing a hydroxyl group. Incorporation of a compound containing a hydroxyl group into the curable composition allows a moderate curing reaction to proceed. Examples of the compound containing a hydroxyl group include ethylene glycol, diethylene glycol, and glycerin. The curable composition according to the present invention may contain one kind, or two or more kinds of the compounds containing a hydroxyl group, such as those described above.

From the viewpoint of improving the heat resistance of the resulting cured product, the content of the compound containing a hydroxyl group in the curable composition according to the present invention is preferably from 0.1 to 10% by mass, and more preferably from 0.2 to 8% by mass.

(10) Other Components

The curable composition according to the present invention may further contain a solvent. Examples of the solvent include methyl ethyl ketone, ethyl acetate, toluene, methanol, and ethanol.

The curable composition according to the present invention may contain various types of additives to the extent that the properties of the composition are not impaired. Examples of the additives include fillers, silane coupling agents, mold release agents, coloring agents, flame retardants, antioxidants, photostabilizers and plasticizers, antifoaming agents, photostabilizers, coloring agents such as pigments and dyes, plasticizers, pH adjusting agents, coloration inhibitors, matting agents, deodorants, weather resistant agents, antistatic agents, yarn friction reducing agents, slip agents, and ion exchangers.

(11) Production of Curable Composition

The curable composition according to the present invention can be produced in accordance with technical common knowledge widely known to those skilled in the art, and the method of producing the curable composition and the components to be further included in the curable composition can be selected as appropriate.

4. Cured Product and Method of Producing the Same

The cured product according to the present invention is one obtained by curing the above described curable composition according to the present invention. The method of curing the curable composition is not particularly limited, and the composition can be cured by heating or irradiation of light, as appropriate.

(1) Conditions for Curing

In cases where the curable composition is cured by heating, the heating of the curable composition is preferably carried out in multiple stages. This allows for a sufficient curing reaction to proceed. For example, the curing reaction can be carried out by performing a first heating at a temperature of from 60 to 120° C. for 10 to 150 minutes, and a second heating at 130 to 200° C. for 60 to 300 minutes. Alternatively, the curing reaction can be carried out, for example, by performing a first heating at a temperature of from 60 to 100° C. from 10 to 150 minutes, a second heating at 120 to 160° C. from 10 to 150 minutes, and a third heating at 180 to 250° C. for 10 to 150 minutes.

Further, in cases where the curable composition is cured by heating, the heating of the curable composition is preferably carried out in multiple stages, taking into consideration the degree of reactivity of the monoepoxy compound according to the present invention. This allows for a sufficient curing reaction to proceed. For example, the curing reaction can be carried out by performing a first heating at a temperature of from 40 to 70° C. for 10 to 150 minutes, a second heating at 71 to 100° C. for 10 to 150 minutes, a third heating at 101 to 140° C. for 10 to 180 minutes, a fourth heating at 141 to 170° C. for 10 to 150 minutes, and a fifth heating at 171 to 220° C. for 10 to 150 minutes. However, the heating conditions are not limited to those described above, and the heating is preferably carried out, varying the conditions as appropriate in view of the content of the monoepoxy compound and the properties of other compounds and the like contained in the curable composition.

In cases where the curable composition is cured by the irradiation of an active energy ray, such as a visible ray, UV light, an X ray, or an electron beam, the type of the active energy ray used and the conditions for irradiation are preferably selected as appropriate, depending on the composition of the curable composition. In one embodiment, it is more preferred that the irradiation of UV light is carried out such that the accumulated amount of light, which is represented as the product of the irradiation intensity and the irradiation time, is adjusted within the range of from 10 to 5,000 mJ/cm$^2$. When the accumulated amount of light irradiated to the curable composition is adjusted within the above described numerical range, it is possible to allow active species derived from the photo-cationic polymerization initiator to be generated sufficiently. This also allows for an improvement in the productivity.

(2) Applications of Cured Product

Specific examples of the application of the curable composition according to the present invention and the cured product obtained therefrom include: adhesive agents, tacky materials; coating materials for coating on substrates such as metals, resin films, glass, paper and wood, surface protective films for semiconductor devices and organic thin film elements (for example, organic electroluminescent elements and organic thin film solar cell elements), hard coating agents, anti-fouling films, and antireflection films; various types of optical members such as lenses, prisms, filters, image display materials, lens arrays, sealing materials and reflector materials for optical semiconductor devices, sealing materials for semiconductor devices, optical waveguides, light guide plates, light diffusion plates, diffraction elements, and optical adhesive agents; and materials such as casting materials, interlayer insulators, insulating films for printed alignment substrates, and fiber-reinforced composite materials.

5. Reactive Diluent

The reactive diluent according to the present invention at least comprises the monoepoxy compound represented by the above described Formula (1). Further, the reactive diluent according to the present invention can be mixed with the other epoxy compound different from the monoepoxy compound. In this case, the mixing ratio of the amount of the monoepoxy compound represented by the above described Formula (1) to the amount of the other epoxy compound different from the monoepoxy compound is preferably from 1:99 to 75:25, and more preferably from 5:95 to 50:50, on a mass basis. When the mixing ratio of the amount of monoepoxy compound to the amount of the other epoxy compound is adjusted within the above described numerical range, it is possible to reduce the viscosity of the resulting mixture to an even lower level, as well as to further improve the heat resistance of a cured product obtained by curing the same.

Aspect I of the present invention, which is one preferred aspect of the present invention, encompasses the following inventions.

(1) A monoepoxy compound represented by the following Formula (1):

[Chem. 9]

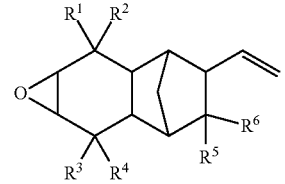

(1)

(wherein $R^1$ to $R^6$ are each independently selected from the group consisting of a hydrogen atom, an alkyl group, and an alkoxy group).

(2) A curable composition comprising: the monoepoxy compound according to (1); the other epoxy compound different from the monoepoxy compound; and a curing agent or a thermal cationic polymerization initiator.

(3) The curable composition according to (2), wherein the content ratio of the monoepoxy compound according to (1) to the other epoxy compound different from the monoepoxy compound, in the curable composition, is from 1:99 to 75:25 on a mass basis.

(4) The curable composition according to (2) or (3), wherein the curing agent is one or more curing agents selected from the group consisting of phenol compounds, amine compounds, acid anhydride-based compounds, and an amide compounds.

(5) The curable composition according to any one of (2) to (4), wherein the other epoxy compound different from the monoepoxy compound is an epoxy resin.

(6) The curable composition according to any one of (2) to (4), wherein the other epoxy compound different from the monoepoxy compound is selected from the group consisting of glycidyl ether-type epoxides, glycidyl ester-type epoxides, and alicyclic epoxides.

(7) The curable composition according to any one of (2) to (4), wherein the thermal cationic polymerization initiator is selected from the group consisting of aromatic sulfonium salt-based thermal cationic polymerization initiators, aromatic iodonium salt-based thermal cationic polymerization initiators, and aluminum complex-based thermal cationic polymerization initiators.

(8) A cured product from the curable composition according to any one of (2) to (7).

(9) A method of producing the monoepoxy compound according to (1), the method comprising the step of allowing a compound represented by the following Formula (2):

[Chem. 10]

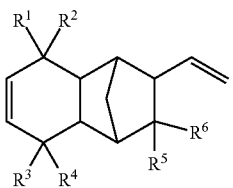

(2)

(wherein $R^1$ to $R^6$ are each independently selected from the group consisting of a hydrogen atom, an alkyl group, and an alkoxy group)
to react with a peracid,
wherein the peracid is used in an amount of from 0.10 to 1.80 mol, with respect to 1.00 mol of the compound represented by the above Formula (2).
(10) The method according to (9), wherein the peracid is hydrogen peroxide or an organic peracid.
(11) A method of producing a cured product, the method comprising the step of curing the curable composition according to any one of (2) to (7).
(12) A reactive diluent comprising at least the monoepoxy compound according to (1).

According to Aspect I of the present invention, it is possible to provide a monoepoxy compound capable of reducing the viscosity of a curable composition containing the monoepoxy compound, while preventing a reduction in the heat resistance of the curable composition as well as a reduction in the weight of the curable composition upon curing.

Aspect II of the present invention, which is one preferred aspect of the present invention, encompasses the following inventions.
(1) A curable composition comprising:
the monoepoxy compound represented by the following Formula (1):

[Chem. 11]

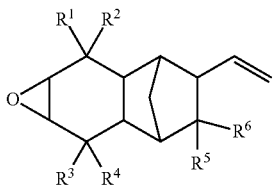

(1)

(wherein $R^1$ to $R^6$ each independently represents a substituent selected from the group consisting of a hydrogen atom, an alkyl group, and an alkoxy group); and a photo-cationic polymerization initiator.
(2) The curable composition according to (1), further comprising the other epoxy compound different from the monoepoxy compound.
(3) The curable composition according to (2), wherein the content ratio of the monoepoxy compound to the other epoxy compound different from the monoepoxy compound, in the curable composition, is from 1:99 to 75:25 on a mass basis.
(4) The curable composition according to (2) or (3), wherein the other epoxy compound different from the monoepoxy compound is selected from the group consisting of glycidyl ether-type epoxies, glycidyl ester-type epoxies, and alicyclic epoxies.
(5) The curable composition according to any one of (1) to (4), wherein the photo-cationic polymerization initiator is an aromatic sulfonium salt-based photo-cationic polymerization initiator.
(6) A cured product from the curable composition according to any one of (1) to (5).

According to Aspect II of the present invention, it is possible to provide a curable composition capable of producing a cured product whose adhesion is dramatically improved.

Aspect III of the present invention, which is one preferred aspect of the present invention, encompasses the following inventions.
(1) A monoepoxy compound comprising a stereoisomer(s) of a compound represented by the following Formula (1), wherein the ratio, as measured by $^{13}$C-NMR analysis, of a peak area(s) derived from a stereoisomer(s) in which the bridgehead of the norbornane skeleton and the vinyl group in the Formula (1) are in a trans relationship, to the total peak area within the chemical shift range of from 140 to 145 ppm, is 66% or more:

[Chem. 12]

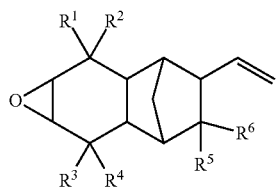

(1)

(wherein $R^1$ to $R^6$ are each independently selected from the group consisting of a hydrogen atom, an alkyl group, and an alkoxy group).
(2) The monoepoxy compound according to (1), wherein $R^1$ to $R^6$ are all hydrogen atoms, and the stereoisomer(s) in which the bridgehead of the norbornane skeleton and the vinyl group are in a trans relationship is/are represented by any of the following Formulae.

[Chem. 13]

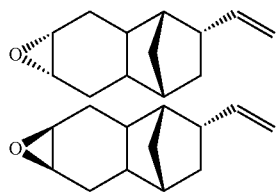

(3) The monoepoxy compound wherein, in the $^{13}$C-NMR analysis of the compound represented by the Formula (1), the ratio of the total peak area within the chemical shift range of from 140 to 142 ppm to the total peak area within the chemical shift range of from 140 to 145 ppm is 66% or more.
(4) The monoepoxy compound according to any one of (1) to (3), wherein, in the $^{13}$C-NMR analysis of the compound represented by the Formula (1), the ratio of the area of the first peak from the low magnetic field side, among peaks within the chemical shift range of from 140 to 142 ppm, to the total peak area within the chemical shift range of from 140 to 145 ppm is 35% or more.

(5) A curable composition comprising: the monoepoxy compound according to any one of (1) to (4); and a thermal cationic polymerization initiator, a photo-cationic polymerization initiator, or a curing agent.

(6) The curable composition according to (5), wherein the curing agent is one or more curing agents selected from the group consisting of phenol-based curing agents, amine-based curing agents, acid anhydride-based curing agents, and amide-based curing agents.

(7) A cured product from the curable composition according to (5) or (6).

According to Aspect III of the present invention, it is possible to provide a monoepoxy compound which allows for the production of a cured product having a high heat resistance.

EXAMPLES

The present invention will now be described in further detail by way of Examples. However, the present invention is in no way limited by these Examples.

I. Examples of Aspect I of the Present Invention

I-1. Example I 1: Synthesis of Monoepoxy Compound (A)

(1) Synthesis of Monoepoxy Compound (A) (Example I 1-1)

Into a reaction vessel equipped with a thermometer, an agitator, a reflux tube and a dropping device, 3,132 g of a diolefin compound represented by the following Formula (3), 3,132 g of toluene and sodium acetate were charged. To the reactor, 3,783 g of a 38% aqueous solution of peracetic acid was added dropwise over five hours, while stirring at −5° C. While continuing to stir the mixture at −5° C., a reaction was allowed to proceed for 17 hours. Subsequently, a 10% aqueous solution of sodium sulfite was used to carry out a neutralization treatment, followed by a liquid separation operation. The resultant was then subjected to distillation at a pressure of 2 hPa and a bottom temperature of from 130 to 140° C., to obtain 2,109 g of a colorless transparent liquid.

In the $^{13}$C-NMR spectrum shown in FIG. 1 and the precise mass measurement by LC-MS, the [M+H]$^+$ of the thus obtained liquid was determined to be 191.1439, which corresponds to the theoretical structure. Accordingly, it was confirmed that the resulting liquid was a monoepoxy compound (A) of interest satisfying the above described Formula (1).

Further, it has been confirmed from the $^{13}$C-NMR spectrum that the stereoisomers represented by Formula (4) and Formula (5) were present as a mixture at a ratio of 75:25. The viscosity of the monoepoxy compound (A) was measured using a Type E viscometer, and determined to be 11.0 mPa·s.

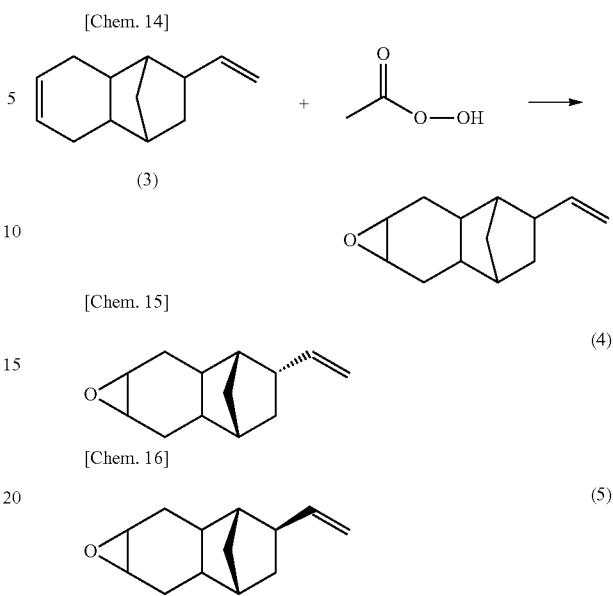

(2) Synthesis of Monoepoxy Compound (A) (Example I 1-2)

Into a screw tube, 0.25 g of apatite and 0.17 g of (CetylPy)$_9$(NH$_4$)[H$_2$W$_{12}$O$_{42}$] were weighed, followed by thorough mixing. To the resulting mixture, 1.21 g of a diolefin compound represented by the following Formula (3), 1.05 g of 35% hydrogen peroxide water, and 0.20 g of toluene were added. After stirring at 20° C. for six hours, 10 mL of toluene was added to the reaction mixture, followed by filtering the mixture. Thereafter, 100 mL of ethyl acetate was used to carry out an operation to separate and extract the filtrate. The organic layer was washed with 30 mL of pure water and 30 mL of saturated saline. After carrying out a dehydration operation with magnesium sulfate, a rotatory evaporator was used to remove the solvent contained therein by distillation. Subsequently, the resultant was subjected to purification by column chromatography, to obtain 0.54 g of the monoepoxy compound (A) of interest satisfying the above described Formula (1).

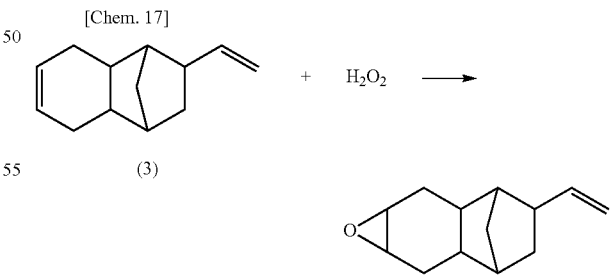

(3) Synthesis of Monoepoxy Compound (A) (Example I 1-3)

Into a reaction vessel equipped with a thermometer, an agitator, a reflux tube and a dropping device, 6.4 g of 35% hydrogen peroxide and 0.36 g of H$_3$PW$_{12}$O$_{40}$ were charged, followed by stirring at 60° C. for 30 minutes. After cooling the resultant at 40° C., 80.11 g of the diolefin compound represented by the above described Formula (3), 0.13 g of cetylpyridinium chloride, and 596 g of chloroform were added thereto. Subsequently, 44.84 g of 35% hydrogen peroxide was added dropwise while stirring at 40° C., and a reaction was allowed proceed at 40° C. for six hours. After the completion of the reaction, 450 g of chloroform was used to carry out a separation and extraction operation. The organic layer was washed with 300 mL of a 10% aqueous solution of sodium thiosulfate, 300 mL of a 10% aqueous solution of sodium carbonate, and 300 mL of pure water. After carrying out a dehydration operation with magnesium sulfate, a rotatory evaporator was used to remove the solvent contained therein by distillation. The resultant was then subjected to distillation at a pressure of 3 hPa and a bottom temperature of from 140 to 160° C., to obtain 50.1 g of the monoepoxy compound (A) of interest represented by the above described Formula (1).

(4) Synthesis of Diepoxy Compound Represented by Formula (6) (Comparative Example I 1-1)

Into a reaction vessel equipped with a thermometer, an agitator, a reflux tube and a dropping device, 8.5 g of a diolefin compound represented by the following Formula (3) and 50 mL of chloroform were charged. To the reactor, 130 mL of an 8% solution of chloroform perbenzoate was added dropwise over five hours, while stirring at −5° C. While continuing to stir the mixture at −5° C., a reaction was allowed to proceed.

Subsequently, a 5% aqueous solution of sodium hydroxide was used to carry out a neutralization treatment, followed by a liquid separation operation. After carrying out a dehydration operation with sodium sulfate, a rotatory evaporator was used to remove the solvent contained therein by distillation. The resultant was then subjected to distillation at a pressure of 1 hPa, to obtain 5.8 g of a diepoxy compound represented by the following Formula (6), as a colorless solid.

[Chem. 18]

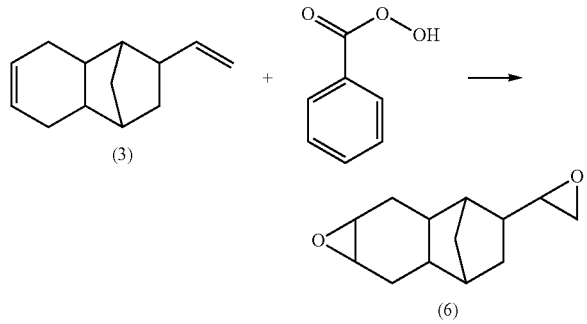

I-2. Example I 2: Preparation of Curable Compositions Containing Monoepoxy Compound (A) and Evaluation Thereof (Part 1: Combination with Epoxy Compound (I B-1) and Curing Agent)

(1) Example I 2-1: Preparation of Curable Composition

A quantity of 13 parts by mass of the monoepoxy compound (A) obtained in Example I 1-1, 100 parts by mass of an epoxy compound (I B-1), 91 parts by mass of a curing agent, and 2 parts by mass of a curing accelerator were mixed to prepare a curable composition.

(2) Comparative Examples I 2-1 to I 2-4

Curable compositions were prepared in the same manner as in Example I 2-1, except that the compositions of the curable compositions were changed as shown in the following Table I-1.

(3) Evaluation of Physical Properties (Viscosity of Curable Composition)

The viscosity of each of the curable compositions obtained in the Example and Comparative Examples was measured using a Type E viscometer. The measurement was carried out at a temperature of 25° C. The measurement results are summarized in Table I-1.

(Weight Reduction Rate of Cured Product from Curable Composition)

The curable compositions obtained in Example I 2-1 and Comparative Examples I 2-1 to I 2-4 were cured by heating in a hot air circulating oven at 100° C. for two hours, and then at 160° C. for four hours, to obtain cured products from the curable compositions. The weight reduction rate of each of the cured products was calculated as follows, and the results are summarized in Table I-1.

Weight reduction rate (%)=(weight of curable composition−weight of cured product from curable composition)/weight of curable composition× 100

(Heat Resistance of Cured Product from Curable Composition)

The glass transition temperature of each of the cured products obtained as described above was measured by increasing the temperature from 30 to 300° C. at a rate of 10° C./min, using a differential scanning calorimeter, DSC7020, manufactured by Hitachi High-Tech Science Corporation, and the thus measured value was taken as the heat resistance of the cured product. The glass transition temperature as used herein refers to a value measured in accordance with JIS K7121, based on "Midpoint Glass Transition Temperature: $T_{mg}$" described in the section of "Method for Measuring Transition Temperature of Plastics". The measurement results are summarized in Table I-1.

(Overall Evaluation)

The overall evaluation of each of the curable compositions obtained in the above described Examples and Comparative Examples was carried out according to the following evaluation criteria. The evaluation results are summarized in Table I-1.

○: The composition has a viscosity of less than 300 mPa·s; and the cure product thereof has a weight reduction rate of less than 5%, and a heat resistance of 140° C. or higher.

Δ: The composition has a viscosity of less than 300 mPa·s; and the cure product thereof has a weight reduction rate of less than 5%, and a heat resistance of 120° C. or higher and less than 140° C.

x: The composition has a viscosity of 300 mPa·s or more; and the cure product thereof has a weight reduction rate of 5% or more, and/or a heat resistance of less than 120° C., and thus has problems in practical use.

TABLE I-1

|  |  |  | Example I 2-1 | Comparative Example I 2-1 | Comparative Example I 2-2 | Comparative Example I 2-3 | Comparative Example I 2-4 |
|---|---|---|---|---|---|---|---|
| Composition (parts by mass) | Epoxy compound (I B-1) |  | 100 | 100 | 100 | 100 | 100 |
|  | Reactive diluent | Monoepoxy compound (A) | 13 |  |  |  |  |
|  |  | I C-1 |  | 5 |  |  |  |
|  |  | I C-2 |  |  | 8 |  |  |
|  |  | I C-3 |  |  |  |  | 10 |
|  | Curing agent |  | 91 | 81 | 88 | 87 | 87 |
|  | Curing accelerator |  | 2 | 2 | 2 | 2 | 2 |
| Viscosity of curable composition (mPa·s) |  |  | 286 | 723 | 277 | 294 | 260 |
| Weight reduction rate of cured product (%) |  |  | 1 | 1 | 2 | 1 | 1 |
| Heat resistance of cured product (° C.) |  |  | 140 | 158 | 135 | 125 | 130 |
| Overall evaluation |  |  | ○ | x | Δ | Δ | Δ |

(Description of Table I-1)

Epoxy compound (I B-1): bisphenol A-type liquid epoxy resin, manufactured by Nippon Steel & Sumikin Chemical Co., Ltd., trade name YD-128

I C-1: butyl glycidyl ether (manufactured by Yokkaichi Chemical Co., Ltd., trade name: DY-BP)

I C-2: 2-ethylhexyl glycidyl ether (manufactured by Yokkaichi Chemical Co., Ltd., trade name: EPOGOSE 2EH)

I C-3: glycidyl ether of a mixture of C12 and C13 alcohols (manufactured by Yokkaichi Chemical Co., Ltd., trade name: EPOGOSE EN)

Curing agent: a mixture of methylhexahydrophthalic anhydride and hexahydrophthalic anhydride, manufactured by New Japan Chemical Co., Ltd., trade name: RIKACID MH-700

Curing accelerator: 2-ethyl-4-methylimidazole, manufactured by Shikoku Chemicals Corporation, trade name: CUREZOL 2E4MZ I-3. Example I 3: Preparation of Curable Compositions Containing Monoepoxy Compound (A) and Evaluation Thereof (Part 2: Combination with Epoxy Compound (I B-2) and Curing Agent)

(1) Example I 3-1

A quantity of 17 parts by mass of the monoepoxy compound (A) obtained in Example I 1-1, 100 parts by mass of an epoxy compound (I B-2), 129 parts by mass of a curing agent, and 2 parts by mass of the curing accelerator were mixed to prepare a curable composition.

(2) Comparative Examples I 3-1 to I 3-4

Curable compositions were prepared in the same manner as in Example I 3-1, except that the compositions of the curable compositions were changed as shown in the following Table I-2.

(3) Evaluation of Physical Properties (Viscosity of Curable Composition)

The viscosity of each of the curable compositions obtained in the Example and Comparative Examples was measured in the same manner as in Example I 2-1. The measurement results are summarized in Table I-2.

(Weight Reduction Rate of Cured Product from Curable Composition)

The curable compositions obtained in Example I 3-1 and Comparative Examples I 3-1 to I 3-4 were cured by heating in a hot air circulating oven at 100° C. for two hours, at 160° C. for two hours, and then at 220° C. for two hours, to obtain cured products from the curable compositions. The weight reduction rate of each of the cured products was calculated in the same manner as in Example I 2-1. The measurement results are summarized in Table I-2.

(Heat Resistance of Cured Product from Curable Composition)

The heat resistance of each of the cured products obtained as described above was measured in the same manner as in Example I 2-1. The measurement results are summarized in Table I-2.

(Overall Evaluation)

The overall evaluation of each of the curable compositions obtained in the above described Example and Comparative Examples was carried out according to the following evaluation criteria. The evaluation results are summarized in Table I-2.

○: The composition has a viscosity of less than 70 mPa·s; and the cure product thereof has a weight reduction rate of less than 5%, and a heat resistance of 200° C. or higher.

Δ: The composition has a viscosity of less than 70 mPa·s; and the cure product thereof has a weight reduction rate of less than 5%, and a heat resistance of 180° C. or higher and less than 200° C.

x: The composition has a viscosity of 70 mPa·s or more; and the cure product thereof has a weight reduction rate of 5% or more, and/or a heat resistance of less than 180° C., and thus has problems in practical use.

TABLE I-2

|  |  |  | Example I 3-1 | Comparative Example I 3-1 | Comparative Example I 3-2 | Comparative Example I 3-3 | Comparative Example I 3-4 |
|---|---|---|---|---|---|---|---|
| Composition (parts by mass) | Epoxy compound (I B-2) | | 100 | 100 | 100 | 100 | 100 |
| | Reactive diluent | Monoepoxy compound (A) | 17 | | | | |
| | | I C-1 | | | 5 | | |
| | | I C-2 | | | | 10 | |
| | | I C-3 | | | | | 10 |
| | Curing agent | | 129 | 115 | 122 | 124 | 122 |
| | Curing accelerator | | 2 | 2 | 2 | 2 | 2 |
| Viscosity of curable composition (mPa·s) | | | 67 | 114 | 65 | 60 | 67 |
| Weight reduction rate of cured product (%) | | | 3 | 1 | 2 | 3 | 1 |
| Heat resistance of cured product (° C.) | | | 209 | 233 | 169 | 184 | 187 |
| Overall evaluation | | | ○ | x | x | Δ | Δ |

(Description of Table I-2)

Epoxy compound (I B-2): 3',4'-epoxycyclohexylmethyl 3,4-epoxycyclohexane carboxylate, manufactured by Daicel Corporation, trade name: CELLOXIDE 2021P I-4. Example I 4: Preparation of Curable Compositions Containing Monoepoxy Compound (A) and Evaluation Thereof (Part 3: Combination with Epoxy Compound (I B-1) and Thermal Cationic Polymerization Initiator)

(1) Example I 4-1

A quantity of 40 parts by mass of the monoepoxy compound (A) obtained in Example I 1-1, 60 parts by mass of the epoxy compound (I B-1), and 1 part by mass of a thermal cationic polymerization initiator were mixed, to prepare a curable composition.

(2) Comparative Examples I 4-1 to I 4-4

Curable compositions were prepared in the same manner as in Example I 4-1, except that the compositions of the curable compositions were changed as shown in the following Table I-3.

(3) Evaluation of Physical Properties (Viscosity of Curable Composition)

The viscosity of each of the curable compositions obtained in the Example and Comparative Examples was measured in the same manner as in Example I 2-1. The measurement results are summarized in Table I-3.

(Weight Reduction Rate of Cured Product from Curable Composition)

The curable compositions obtained in Example I 4-1 and Comparative Examples I 4-1 to I 4-4 were cured by heating in a hot air circulating oven at 80° C. for two hours, at 120° C. for two hours, and then at 180° C. for two hours, to obtain cured products from the curable compositions. The weight reduction rate of each of the cured products was calculated in the same manner as in Example I 2-1. The measurement results are summarized in Table I-3.

(Heat Resistance of Cured Product from Curable Composition)

The heat resistance of each of the cured products obtained as described above was measured in the same manner as in Example I 2-1. The measurement results are summarized in Table I-3.

(Overall Evaluation)

The overall evaluation of each of the curable compositions obtained in the above described Example and Comparative Examples was carried out according to the following evaluation criteria. The evaluation results are summarized in Table I-3.

○: The composition has a viscosity of less than 300 mPa·s; and the cure product therefrom has a weight reduction rate of less than 5%, and a heat resistance of 130° C. or higher.

Δ: The composition has a viscosity of less than 300 mPa·s; and the cure product therefrom has a weight reduction rate of less than 5%, and a heat resistance of 110° C. or higher and less than 130° C.

x: The composition has a viscosity of 300 mPa·s or more; and the cure product therefrom has a weight reduction rate of 5% or more, and/or a heat resistance of less than 110° C., and thus has problems in practical use.

TABLE I-3

|  |  |  | Example I 4-1 | Comparative Example I 4-1 | Comparative Example I 4-2 | Comparative Example I 4-3 | Comparative Example I 4-4 |
|---|---|---|---|---|---|---|---|
| Composition (parts by mass) | Epoxy compound (I B-1) | | 60 | 100 | 60 | 60 | 60 |
| | Reactive diluent | Monoepoxy compound (A) | 40 | | | | |
| | | I C-1 | | | 40 | | |
| | | I C-2 | | | | 40 | |
| | | I C-4 | | | | | 40 |

TABLE I-3-continued

|  | Example I 4-1 | Comparative Example I 4-1 | Comparative Example I 4-2 | Comparative Example I 4-3 | Comparative Example I 4-4 |
| --- | --- | --- | --- | --- | --- |
| Thermal cationic polymerization initiator | 1 | 1 | 1 | 1 | 1 |
| Viscosity of curable composition (mPa · s) | 298 | 5360 | 21 | 47 | 32 |
| Weight reduction rate of cured product (%) | 0 | 0 | 36 | 28 | 29 |
| Heat resistance of cured product (° C.) | 136 | 156 | 116 | 77 | 150 |
| Overall evaluation | ∘ | x | x | x | x |

(Description of Table I-3)

I C-4: 1,2-epoxy-4-vinylcyclohexane (manufactured by Daicel Corporation, trade name: CELLOXIDE 2000)

Thermal cationic polymerization initiator: aromatic sulfonium salt, manufactured by Sanshin Chemical Industry Co., Ltd., trade name: SI-80L

I-5. Example I 5: Preparation of Curable Compositions Containing Monoepoxy Compound (A) and Evaluation Thereof (Part 4: Combination with Epoxy Compound (I B-2) and Thermal Cationic Polymerization Initiator)

(1) Example I 5-1

A quantity of 50 parts by mass of the monoepoxy compound (A) obtained in Example I 1-1, 50 parts by mass of the epoxy compound (I B-2), and 1 part by mass of the thermal cationic polymerization initiator were mixed, to prepare a curable composition.

(2) Comparative Examples I 5-1 to I 5-4

Curable compositions were prepared in the same manner as in Example I 5-1, except that the compositions of the curable compositions were changed as shown in the following Table I-4.

(3) Evaluation of Physical Properties (Viscosity of Curable Composition)

The viscosity of each of the curable compositions obtained in the Example and Comparative Examples was measured in the same manner as in Example I 2-1. The measurement results are summarized in Table I-4.

(Weight Reduction Rate of Cured Product from Curable Composition)

The curable compositions obtained in Example I 5-1 and Comparative Examples I 5-1 to I 5-4 were cured by heating in a hot air circulating oven at 60° C. for two hours, at 80° C. for two hours, at 120° C. for one hour, at 150° C. for one hour, and then at 180° C. for one hour, to obtain cured products from the curable compositions. The weight reduction rate of each of the cured products was calculated in the same manner as in Example I 2-1. The measurement results are summarized in Table I-4.

(Heat Resistance of Cured Product from Curable Composition)

The heat resistance of each of the cured products obtained as described above was measured in the same manner as in Example I 2-1. The measurement results are summarized in Table I-4.

(Overall Evaluation)

The overall evaluation of each of the curable compositions obtained in the above described Example and Comparative Examples was carried out according to the following evaluation criteria. The evaluation results are summarized in Table I-4.

∘: The composition has a viscosity of less than 70 mPa·s; and the cure product therefrom has a weight reduction rate of less than 5%, and a heat resistance of 150° C. or higher.

Δ: The composition has a viscosity of less than 70 mPa·s; and the cure product therefrom has a weight reduction rate of less than 5%, and a heat resistance of 130° C. or higher and less than 150° C.

x: The composition has a viscosity of 70 mPa·s or more; and the cure product therefrom has a weight reduction rate of 5% or more, and/or a heat resistance of less than 130° C., and thus has problems in practical use.

TABLE I-4

|  |  |  | Example I 5-1 | Comparative Example I 5-1 | Comparative Example I 5-2 | Comparative Example I 5-3 | Comparative Example I 5-4 |
| --- | --- | --- | --- | --- | --- | --- | --- |
| Composition (parts by mass) | Epoxy compound (I B-2) |  | 50 | 100 | 50 | 50 | 50 |
|  | Reactive diluent | Monoepoxy compound (A) | 50 |  |  |  |  |
|  |  | I C-1 |  |  | 50 |  |  |
|  |  | I C-2 |  |  |  | 50 |  |
|  |  | I C-4 |  |  |  |  | 50 |
|  | Thermal cationic polymerization initiator |  | 1 | 1 | 1 | 1 | 1 |

TABLE I-4-continued

|  | Example I 5-1 | Comparative Example I 5-1 | Comparative Example I 5-2 | Comparative Example I 5-3 | Comparative Example I 5-4 |
|---|---|---|---|---|---|
| Viscosity of curable composition (mPa · s) | 42 | 199 | 7 | 12 | 7 |
| Weight reduction rate of cured product (%) | 0 | 0 | 31 | 7 | 16 |
| Heat resistance of cured product (° C.) | 156 | 187 | 185 | 154 | 155 |
| Overall evaluation | ○ | x | x | x | x |

I-6. Example I 6: Preparation of Curable Compositions Containing Monoepoxy Compound (A) and Evaluation Thereof (Part 5: Combination with Various Types of Epoxy Compounds and Thermal Cationic Polymerization Initiator)

(1) Examples I 6-1 to I 6-6 and Comparative Examples I 6-1 to I 6-12

Curable compositions were prepared in the same manner as in Example I 2-1, except that the following components were used, at the compositions shown in Tables I-5 to 1-7.
(i) Epoxy Compound (I B-2)
3',4'-Epoxycyclohexylmethyl 3,4-epoxycyclohexane carboxylate, manufactured by Daicel Corporation, trade name: CELLOXIDE 2021P, was used.
(ii) Epoxy Compound (I B-4)
A phenol novolac type epoxy resin, manufactured by Nippon Steel & Sumikin Chemical Co., Ltd., trade name: YDPN-638, was used.
(iii) Epoxy Compound (I B-6)
A hydrogenated bisphenol A-type liquid epoxy resin, manufactured by Mitsubishi Chemical Corporation, trade name: YX8000, was used.
(iv) Epoxy Compound (I B-9)
Cyclohexanedicarboxylic acid diglycidyl ester, a reagent manufactured by Tokyo Chemical Industry Co., Ltd. was used.
(v) Epoxy Compound (I B-10)
Vinylcyclohexene dioxide, a reagent manufactured by Sigma-Aldrich Co. was used.
(vi) Epoxy Compound (I B-11)
1,2-Epoxy-(2-oxiranyl)cyclohexane adduct of 2,2-bis(hydroxymethyl)-1-butanol, manufactured by Daicel Corporation, trade name: EHPE 3150, was used.
(vii) Epoxy Compound (I B-12)
(3,3',4,4'-Diepoxy)bicyclohexyl, manufactured by Daicel Corporation, trade name: CELLOXIDE 8000, was used.
(viii) Monoepoxy Compound (A)
The monoepoxy compound (A) obtained in Example I 1-1 was used.
(ix) Reactive Diluent (I C-2)
2-Ethylhexyl glycidyl ether, manufactured by Yokkaichi Chemical Co., Ltd., trade name: EPOGOSE 2EH, was used.
(x) Thermal Cationic Polymerization Initiator (I E-2)
4-Acetoxyphenyldimethylsulfonium hexafluoroantimonate, manufactured by Sanshin Chemical Industry Co., Ltd., trade name: SI-150L, was used.

(2) Evaluation of Physical Properties (Viscosity of Curable Composition) The viscosity of each of the curable compositions obtained in the Examples and Comparative Examples was measured in the same manner as in Example I 2-1. The measurement results are summarized in Tables I-5 to 1-7.
(Weight Reduction Rate of Cured Product from Curable Composition)
The curable compositions obtained as described above were heated under the following respective conditions, to obtain cured products.

(a) Example I 6-1

The curable composition obtained as described above was cured by heating in a hot air circulating oven at 150° C. for one hour, at 180° C. for one hour, at then at 240° C. for two hours, to obtain a cured product from the curable composition.

(b) Example I 6-2

The curable composition obtained as described above was cured by heating in a hot air circulating oven at 120° C. for one hour, and then at 220° C. for two hours, to obtain a cured product from the curable composition.

(c) Example I 6-3

The curable composition obtained as described above was cured by heating in a hot air circulating oven at 150° C. for one hour, at 170° C. for one hour, and then at 210° C. for two hours, to obtain a cured product from the curable composition.

(d) Example I 6-4

The curable composition obtained as described above was cured by heating in a hot air circulating oven at 120° C. for one hour, and then at 220° C. for two hours, to obtain a cured product from the curable composition.

(e) Example I 6-5

The curable composition obtained as described above was cured by heating in a hot air circulating oven at 110° C. for one hour, at 170° C. for one hour, and then at 220° C. for two hours, to obtain a cured product from the curable composition.

(f) Example I 6-6

The curable composition obtained as described above was cured by heating in a hot air circulating oven at 110° C. for one hour, at 130° C. for one hour, and then at 220° C. for two hours, to obtain a cured product from the curable composition.

(a') Comparative Example I 6-1

The curable composition obtained as described above was cured by heating in a hot air circulating oven at 150° C. for one hour, at 180° C. for one hour, at then at 240° C. for two hours, to obtain a cured product from the curable composition.

(b') Comparative Example I 6-2

The curable composition obtained as described above was cured by heating in a hot air circulating oven at 150° C. for one hour, at 180° C. for one hour, at then at 240° C. for two hours, to obtain a cured product from the curable composition.

(c') Comparative Example I 6-3

The curable composition obtained as described above was cured by heating in a hot air circulating oven at 120° C. for one hour, and then at 220° C. for two hours, to obtain a cured product from the curable composition.

(d') Comparative Example I 6-4

The curable composition obtained as described above was cured by heating in a hot air circulating oven at 120° C. for one hour, and then at 220° C. for two hours, to obtain a cured product from the curable composition.

(e') Comparative Example I 6-5

The curable composition obtained as described above was cured by heating in a hot air circulating oven at 150° C. for one hour, at 170° C. for one hour, and then at 210° C. for two hours, to obtain a cured product from the curable composition.

(f') Comparative Example I 6-6

The curable composition obtained as described above was cured by heating in a hot air circulating oven at 150° C. for one hour, at 170° C. for one hour, and then at 210° C. for two hours, to obtain a cured product from the curable composition.

(g') Comparative Example I 6-7

The curable composition obtained as described above was cured by heating in a hot air circulating oven at 120° C. for one hour, and then at 220° C. for two hours, to obtain a cured product from the curable composition.

(h') Comparative Example I 6-8

The curable composition obtained as described above was cured by heating in a hot air circulating oven at 120° C. for one hour, and then at 220° C. for two hours, to obtain a cured product from the curable composition.

(i') Comparative Example I 6-9

The curable composition obtained as described above was cured by heating in a hot air circulating oven at 110° C. for one hour, at 170° C. for one hour, and then at 220° C. for two hours, to obtain a cured product from the curable composition.

(j') Comparative Example I 6-10

The curable composition obtained as described above was cured by heating in a hot air circulating oven at 110° C. for one hour, at 170° C. for one hour, and then at 220° C. for two hours, to obtain a cured product from the curable composition.

(k') Comparative Example I 6-11

The curable composition obtained as described above was cured by heating in a hot air circulating oven at 110° C. for one hour, at 130° C. for one hour, and then at 220° C. for two hours, to obtain a cured product from the curable composition.

(l') Comparative Example I 6-12

The curable composition obtained as described above was cured by heating in a hot air circulating oven at 110° C. for one hour, at 130° C. for one hour, and then at 220° C. for two hours, to obtain a cured product from the curable composition.

The weight reduction rate of each of the cured products obtained as described above was calculated in the same manner as in Example I 2-1. The measurement results are summarized in Tables I-5 to 1-7.
(Heat Resistance of Cured Product from Curable Composition)

The heat resistance of each of the cured products obtained as described above was measured in the same manner as in Example I 2-1. The measurement results are summarized in Tables I-5 to 1-7.
(Overall Evaluation)

The overall evaluation of each of the curable compositions obtained in the above described Examples I 6-1 to I 6-6 and Comparative Examples I 6-1 to I 6-12 was carried out according to the following evaluation criteria, using the measurement results of the viscosity, weight reduction rate, and heat resistance summarized in Tables I-5 to 1-7, and using the reference values for the viscosity, weight reduction rate, and heat resistance, defined common to the Examples and the corresponding Comparative Examples in each of the experimental sections, shown in Tables I-5 to 1-7. The evaluation results are summarized in Tables I-5 to 1-7.
Evaluation Criteria Evaluation of viscosity: when the measurement result of the viscosity of each curable composition is equal to or less than the reference value shown for each experimental section in each Table, it is taken that the evaluation criterion for the viscosity is satisfied.

Evaluation of weight reduction rate: when the measurement result of the weight reduction rate of each cured product is equal to or less than the reference value shown for each experimental section in each Table, it is taken that the evaluation criterion for the weight reduction rate is satisfied.

Evaluation of heat resistance: when the measurement result of the heat resistance of each cured product is equal to or more than the reference value shown for each experimental section in each Table, it is taken that the evaluation criterion for the heat resistance is satisfied.

Overall evaluation: when all of the above described three evaluation criteria are satisfied, the overall evaluation for the composition and the cured product thereof is determined as "o".

TABLE I-5

| | | Example I 6-1 | Example I 6-2 | Comparative Example I 6-1 | Comparative Example I 6-2 | Comparative Example I 6-3 | Comparative Example I 6-4 |
|---|---|---|---|---|---|---|---|
| Composition (parts by mass) | Epoxy compound (I B-4) | 60 | | 100 | 60 | | |
| | Epoxy compound (I B-6) | | 60 | | | 100 | 60 |
| | Monoepoxy compound (A) | 40 | 40 | | | | |
| | Reactive diluent (I C-2) | | | | 40 | | 40 |
| | Thermal cationic polymerization initiator (I E-2) | 2 | 2 | 2 | 2 | 2 | 2 |
| Viscosity of curable composition (mPa·s) | | 2089 | 97 | Solid | 246 | 2005 | 22 |
| Reference value for viscosity (mPa·s) | | 2500 | 100 | 2500 | 2500 | 100 | 100 |
| Weight reduction rate of cured product (%) | | 7 | 6 | 0 | 15 | 4 | 16 |
| Reference value for weight reduction rate (%) | | 10 | 15 | 10 | 10 | 15 | 15 |
| Heat resistance of cured product (°C) | | 160 | 145 | 130 | 117 | 148 | 113 |
| Reference value for heat resistance (°C) | | 150 | 90 | 150 | 150 | 90 | 90 |
| Overall evaluation | | ○ | ○ | x | x | x | x |

TABLE I-6

| | | Example I 6-3 | Example I 6-4 | Comparative Example I 6-5 | Comparative Example I 6-6 | Comparative Example I 6-7 | Comparative Example I 6-8 |
|---|---|---|---|---|---|---|---|
| Composition (parts by mass) | Epoxy compound (I B-9) | 60 | | 100 | 60 | | |
| | Epoxy compound (I B-10) | | 60 | | | 100 | 60 |
| | Monoepoxy compound (A) | 40 | 40 | | | | |
| | Reactive diluent (I C-2) | | | | 40 | | 40 |
| | Thermal cationic polymerization initiator (I E-2) | 2 | 2 | 2 | 2 | 2 | 2 |
| Viscosity of curable composition (mPa·s) | | 73 | 7 | 489 | 17 | 6 | 4 |
| Reference value for viscosity (mPa·s) | | 100 | 100 | 100 | 100 | 100 | 100 |
| Weight reduction rate of cured product (%) | | 16 | 13 | 1 | 26 | 29 | 23 |
| Reference value for weight reduction rate (%) | | 20 | 20 | 20 | 20 | 20 | 20 |
| Heat resistance of cured product (°C) | | 113 | 103 | 90 | 112 | 236 | 85 |
| Reference value for heat resistance (°C) | | 100 | 100 | 100 | 100 | 100 | 100 |
| Overall evaluation | | ○ | ○ | x | x | x | x |

TABLE I-7

| | | Example I 6-5 | Example I 6-6 | Comparative Example I 6-9 | Comparative Example I 6-10 | Comparative Example I 6-11 | Comparative Example I 6-12 |
|---|---|---|---|---|---|---|---|
| Composition (parts by mass) | Epoxy compound (I B-2) | 30 | | 50 | 30 | | |
| | Epoxy compound (I B-II) | 30 | | 50 | 30 | | |
| | Epoxy compound (I B-12) | | 60 | | | 100 | 60 |
| | Monoepoxy compound (A) | 40 | 40 | | | | |
| | Reactive diluent (I C-2) | | | | 40 | | 40 |
| | Thermal cationic polymerization initiator (I E-2) | 2 | 2 | 2 | 2 | 2 | 2 |
| Viscosity of curable composition (mPa · s) | | 328 | 24 | 19620 | 56 | 45 | 8 |
| Reference value for viscosity (mPa · s) | | 400 | 400 | 400 | 400 | 400 | 400 |
| Weight reduction rate of cured product (%) | | 1 | 1 | 0 | 10 | 4 | 8 |
| Reference value for weight reduction rate (%) | | 5 | 5 | 5 | 5 | 5 | 5 |
| Heat resistance of cured product (° C.) | | 250 | 218 | 199 | 241 | 225 | 228 |
| Reference value for heat resistance (° C.) | | 200 | 200 | 200 | 200 | 200 | 200 |
| Overall evaluation | | ○ | ○ | x | x | x | x |

I-7. Example I 7: Preparation of Curable Compositions Containing Monoepoxy Compound (A) and Evaluation Thereof (Part 6: Combination with Various Types of Oxetane Compounds and Thermal Cationic Polymerization Initiator)

(1) Examples I 7-1 to I 7-4 and Comparative Examples I 7-1 to I 7-8

Curable compositions were prepared in the same manner as in Example I 2-1, except that the following components were used, at the compositions shown in Tables I-8 and 1-9.
(i) Epoxy Compound (I B-1)
A bisphenol A-type liquid epoxy resin, manufactured by Nippon Steel & Sumikin Chemical Co., Ltd., trade name: YD-128, was used.
(ii) Monoepoxy Compound (A)
The monoepoxy compound (A) obtained in Example I 1-1 was used.
(iii) Reactive Diluent (I C-2)
2-Ethylhexyl glycidyl ether, manufactured by Yokkaichi Chemical Co., Ltd., trade name: EPOGOSE 2EH, was used.
(iv) Oxetane Compound (I D-1)
1,4-Bis[(3-ethyl-3-oxetanylmethoxy)methyl]benzene, manufactured by Toagosei Co., Ltd., trade name: ARONE OXETANE OXT-121, was used.
(v) Oxetane Compound (I D-2)
3-Ethyl-3-hydroxymethyloxetane, manufactured by Toagosei Co., Ltd., trade name: ARONE OXETANE OXT-101, was used.
(vi) Oxetane Compound (I D-3)
Di[(3-ethyl-3-oxetanyl)methyl]ether, manufactured by Toagosei Co., Ltd., trade name: ARONE OXETANE OXT-221, was used.
(vii) Oxetane Compound (I D-4)
3-Ethyl-3-(2-ethylhexyloxymethyl)oxetane, manufactured by Toagosei Co., Ltd., trade name: ARONE OXETANE OXT-212, was used.
(viii) Thermal Cationic Polymerization Initiator (I E-2)
4-Acetoxyphenyldimethylsulfonium hexafluoroantimonate, manufactured by Sanshin Chemical Industry Co., Ltd., trade name: SI-150L, was used.

(2) Evaluation of Physical Properties (Viscosity of Curable Composition)
The viscosity of each of the curable compositions obtained in the Examples and Comparative Examples was measured in the same manner as in Example I 2-1. The measurement results are summarized in Tables I-8 and 1-9.
(Weight Reduction Rate of Cured Product from Curable Composition)
The curable compositions obtained as described above were heated under the following respective conditions, to obtain cured products.

(a) Example I 7-1

The curable composition obtained as described above was cured by heating in a hot air circulating oven at 120° C. for one hour, at 140° C. for one hour, and then at 220° C. for two hours, to obtain a cured product from the curable composition.

(b) Example I 7-2

The curable composition obtained as described above was cured by heating in a hot air circulating oven at 110° C. for one hour, at 150° C. for one hour, and then at 220° C. for two hours, to obtain a cured product from the curable composition.

(c) Example I 7-3

The curable composition obtained as described above was cured by heating in a hot air circulating oven at 110° C. for one hour, at 130° C. for one hour, and then at 220° C. for two hours, to obtain a cured product from the curable composition.

(d) Example I 7-4

The curable composition obtained as described above was cured by heating in a hot air circulating oven at 120° C. for one hour, at 170° C. for one hour, and then at 220° C. for two hours, to obtain a cured product from the curable composition.

(a') Comparative Example I 7-1

The curable composition obtained as described above was cured by heating in a hot air circulating oven at 120° C. for one hour, at 140° C. for one hour, and then at 220° C. for two hours, to obtain a cured product from the curable composition.

(b') Comparative Example I 7-2

The curable composition obtained as described above was cured by heating in a hot air circulating oven at 120° C. for one hour, at 140° C. for one hour, and then at 220° C. for two hours, to obtain a cured product from the curable composition.

(c') Comparative Example I 7-3

The curable composition obtained as described above was cured by heating in a hot air circulating oven at 110° C. for one hour, at 150° C. for one hour, and then at 220° C. for two hours, to obtain a cured product from the curable composition.

(d') Comparative Example I 7-4

The curable composition obtained as described above was cured by heating in a hot air circulating oven at 110° C. for one hour, at 150° C. for one hour, and then at 220° C. for two hours, to obtain a cured product from the curable composition.

(e') Comparative Example I 7-5

The curable composition obtained as described above was cured by heating in a hot air circulating oven at 110° C. for one hour, at 130° C. for one hour, and then at 220° C. for two hours, to obtain a cured product from the curable composition.

(f') Comparative Example I 7-6

The curable composition obtained as described above was cured by heating in a hot air circulating oven at 110° C. for one hour, at 130° C. for one hour, and then at 220° C. for two hours, to obtain a cured product from the curable composition.

(g') Comparative Example I 7-7

The curable composition obtained as described above was cured by heating in a hot air circulating oven at 120° C. for one hour, at 170° C. for one hour, and then at 220° C. for two hours, to obtain a cured product from the curable composition.

(h') Comparative Example I 7-8

The curable composition obtained as described above was cured by heating in a hot air circulating oven at 120° C. for one hour, at 170° C. for one hour, and then at 220° C. for two hours, to obtain a cured product from the curable composition.

The weight reduction rate of each of the cured products obtained as described above was calculated in the same manner as in Example I 2-1. The measurement results are summarized in Tables I-8 and I-9.

(Heat Resistance of Cured Product from Curable Composition)

The heat resistance of each of the cured products obtained as described above was measured in the same manner as in Example I 2-1. The measurement results are summarized in Tables I-8 and I-9.

Overall Evaluation

The overall evaluation of each of the curable compositions obtained in the above described Examples I 7-1 to I 7-4 and Comparative Examples I 7-1 to I 7-8 was carried out according to the following evaluation criteria, using the measurement results of the viscosity, weight reduction rate, and heat resistance summarized in Tables I-8 and I-9, and using the reference values for the viscosity, weight reduction rate, and heat resistance, defined common to the Examples and the corresponding Comparative Examples in each of the experimental sections, shown in Tables I-8 and I-9. The evaluation results are summarized in Tables I-8 and I-9.

Evaluation Criteria

Evaluation of viscosity: when the measurement result of the viscosity of each curable composition is equal to or less than the reference value shown for each experimental section in each Table, it is taken that the evaluation criterion for the viscosity is satisfied.

Evaluation of weight reduction rate: when the measurement result of the weight reduction rate of each cured product is equal to or less than the reference value shown for each experimental section in each Table, it is taken that the evaluation criterion for the weight reduction rate is satisfied.

Evaluation of heat resistance: when the measurement result of the heat resistance of each cured product is equal to or more than the reference value shown for each experimental section in each Table, it is taken that the evaluation criterion for the heat resistance is satisfied.

Overall evaluation: when all of the above described three evaluation criteria are satisfied, the overall evaluation for the composition and the cured product therefrom is determined as "o".

TABLE I-8

| | | Example I 7-1 | Example I 7-2 | Comparative Example I 7-1 | Comparative Example I 7-2 | Comparative Example I 7-3 | Comparative Example I 7-4 |
|---|---|---|---|---|---|---|---|
| Composition (parts by mass) | Epoxy compound (I B-I) | 45 | 45 | 75 | 45 | 75 | 45 |
| | Monoepoxy compound (A) | 40 | 40 | | | | |
| | Reactive diluent (I C-2) | | | | 40 | | 40 |
| | Oxetane compound (I D-1) | 15 | | 25 | 15 | | |
| | Oxetane compound (I D-2) | | 15 | | | 25 | 15 |
| | Thermal cationic polymerization initiator (I E-2) | 2 | 2 | 2 | 2 | 2 | 2 |
| Viscosity of curable composition (mPa·s) | | 63 | 85 | 284 | 18 | 455 | 21 |
| Reference value for viscosity (mPa·s) | | 100 | 100 | 100 | 100 | 100 | 100 |
| Weight reduction rate of cured product (%) | | 13 | 16 | 9 | 20 | 11 | 24 |
| Reference value for weight reduction rate (%) | | 15 | 20 | 15 | 15 | 20 | 20 |
| Heat resistance of cured product (°C.) | | 93 | 125 | 175 | 113 | 145 | 132 |
| Reference value for heat resistance (°C.) | | 90 | 100 | 90 | 90 | 100 | 100 |
| Overall evaluation | | ○ | ○ | x | x | x | x |

TABLE I-9

| | | Example I 7-3 | Example I 7-4 | Comparative Example I 7-5 | Comparative Example I 7-6 | Comparative Example I 7-7 | Comparative Example I 7-8 |
|---|---|---|---|---|---|---|---|
| Composition (parts by mass) | Epoxy compound (I B-1) | 45 | 45 | 75 | 45 | 75 | 45 |
| | Monoepoxy compound (A) | 40 | 40 | | | | |
| | Reactive diluent (I C-2) | | | | 40 | | 40 |
| | Oxetane compound (I D-3) | 15 | | 25 | 15 | | |
| | Oxetane compound (I D-4) | | 15 | | | 25 | 15 |
| | Thermal cationic polymerization initiator (I E-2) | 2 | 2 | 2 | 2 | 2 | 2 |
| Viscosity of curable composition (mPa·s) | | 82 | 63 | 588 | 22 | 269 | 17 |
| Reference value for viscosity (mPa·s) | | 100 | 100 | 100 | 100 | 100 | 100 |
| Weight reduction rate of cured product (%) | | 7 | 11 | 2 | 19 | 8 | 22 |
| Reference value for weight reduction rate (%) | | 15 | 15 | 15 | 15 | 15 | 15 |
| Heat resistance of cured product (°C.) | | 130 | 98 | 160 | 121 | 124 | 114 |
| Reference value for heat resistance (°C.) | | 90 | 90 | 90 | 90 | 90 | 90 |
| Overall evaluation | | ○ | ○ | x | x | x | x |

I-8. Example I 8: Preparation of Curable Compositions Containing Monoepoxy Compound (A) and Evaluation Thereof (Part 7: Combination with Various Types of Thermal Cationic Polymerization Initiators)

(1) Examples I 8-1 to I 8-4 and Comparative Examples I 8-1 to I 8-8

Curable compositions were prepared in the same manner as in Example I 2-1, except that the following components were used, at the compositions shown in Tables I-10 and I-11.

(i) Epoxy Compound (I B-1)

A bisphenol A-type liquid epoxy resin, manufactured by Nippon Steel & Sumikin Chemical Co., Ltd., trade name: YD-128, was used.

(ii) Monoepoxy Compound (A)

The monoepoxy compound (A) obtained in Example I 1-1 was used.

(iii) Reactive Diluent (I C-2)

2-Ethylhexyl glycidyl ether, manufactured by Yokkaichi Chemical Co., Ltd., trade name: EPOGOSE 2EH, was used.

(iv) Thermal Cationic Polymerization Initiator (I E-3)

4-Hydroxyphenylbenzylmethylsulfonium hexafluoroantimonate, manufactured by Sanshin Chemical Industry Co., Ltd., trade name: SI-100L, was used.

(v) Thermal Cationic Polymerization Initiator (I E-4)

Bis[4-(di(4-(2-hydroxyethoxy))phenylsulfonio)phenyl] sulfide bishexafluoroantimonate, manufactured by ADEKA CORPORATION, ADEKA ARKLS SP-170, was used.

(vi) Thermal Cationic Polymerization Initiator (I E-5)

Diphenyl-4-(phenylthio)phenylsulfonium hexafluoroantimonate, manufactured by San-Apro Ltd., CPI-101A, was used.

(vii) Thermal Cationic Polymerization Initiator (I E-6)

4-Methylphenyl-4-(1-methylethyl)phenyliodonium tetrakis(pentafluorophenyl)borate, a reagent manufactured by Tokyo Chemical Industry Co., Ltd. was used.

(2) Evaluation of Physical Properties (Viscosity of Curable Composition)
The viscosity of each of the curable compositions obtained in the Examples and Comparative Examples was measured in the same manner as in Example I 2-1. The measurement results are summarized in Tables I-10 and I-11.

(Weight Reduction Rate of Cured Product from Curable Composition)

The curable compositions obtained as described above were heated under the following respective conditions, to obtain cured products.

(a) Example I 8-1

The curable composition obtained as described above was cured by heating in a hot air circulating oven at 115° C. for one hour, at 130° C. for one hour, at 190° C. for one hour, and then at 240° C. for two hours, to obtain a cured product from the curable composition.

(b) Example I 8-2

The curable composition obtained as described above was cured by heating in a hot air circulating oven at 120° C. for one hour, and then at 240° C. for two hours, to obtain a cured product from the curable composition.

(c) Example I 8-3

The curable composition obtained as described above was cured by heating in a hot air circulating oven at 80° C. for one hour, at 140° C. for one hour, and then at 180° C. for two hours, to obtain a cured product from the curable composition.

(d) Example I 8-4

The curable composition obtained as described above was cured by heating in a hot air circulating oven at 140° C. for one hour, at 160° C. for one hour, and then at 240° C. for two hours, to obtain a cured product from the curable composition.

(a') Comparative Example I 8-1

The curable composition obtained as described above was cured by heating in a hot air circulating oven at 115° C. for one hour, at 130° C. for one hour, at 190° C. for one hour, and then at 240° C. for two hours, to obtain a cured product from the curable composition.

(b') Comparative Example I 8-2

The curable composition obtained as described above was cured by heating in a hot air circulating oven at 115° C. for one hour, at 130° C. for one hour, at 190° C. for one hour, and then at 240° C. for two hours, to obtain a cured product from the curable composition.

(c') Comparative Example I 8-3

The curable composition obtained as described above was cured by heating in a hot air circulating oven at 120° C. for one hour, and then at 240° C. for two hours, to obtain a cured product from the curable composition.

(d') Comparative Example I 8-4

The curable composition obtained as described above was cured by heating in a hot air circulating oven at 120° C. for one hour, and then at 240° C. for two hours, to obtain a cured product from the curable composition.

(e') Comparative Example I 8-5

The curable composition obtained as described above was cured by heating in a hot air circulating oven at 80° C. for one hour, at 140° C. for one hour, and then at 180° C. for two hours, to obtain a cured product from the curable composition.

(f') Comparative Example I 8-6

The curable composition obtained as described above was cured by heating in a hot air circulating oven at 80° C. for one hour, at 140° C. for one hour, and then at 180° C. for two hours, to obtain a cured product from the curable composition.

(g') Comparative Example I 8-7

The curable composition obtained as described above was cured by heating in a hot air circulating oven at 140° C. for one hour, at 160° C. for one hour, and then at 240° C. for two hours, to obtain a cured product from the curable composition.

(h') Comparative Example I 8-8

The curable composition obtained as described above was cured by heating in a hot air circulating oven at 140° C. for one hour, at 160° C. for one hour, and then at 240° C. for two hours, to obtain a cured product from the curable composition.

The weight reduction rate of each of the cured products obtained as described above was calculated in the same manner as in Example I 2-1. The measurement results are summarized in Tables I-10 and I-11.

(Heat Resistance of Cured Product from Curable Composition)

The heat resistance of each of the cured products obtained as described above was measured in the same manner as in Example I 2-1. The measurement results are summarized in Tables I-10 and I-11.

(Overall Evaluation)

The overall evaluation of each of the curable compositions obtained in the above described Examples I 8-1 to I 8-4 and Comparative Examples I 8-1 to I 8-8 was carried out according to the following evaluation criteria, using the measurement results of the viscosity, weight reduction rate, and heat resistance summarized in Tables I-10 and I-11, and using the reference values for the viscosity, weight reduction rate, and heat resistance, defined common to the Examples and the corresponding Comparative Examples in each of the experimental sections, shown in Tables I-10 and I-11. The evaluation results are summarized in Tables I-10 and I-11.

Evaluation Criteria

Evaluation of viscosity: when the measurement result of the viscosity of each curable composition is equal to or less than the reference value shown for each experimental section in each Table, it is taken that the evaluation criterion for the viscosity is satisfied.

Evaluation of weight reduction rate: when the measurement result of the weight reduction rate of each cured product is equal to or less than the reference value shown for each experimental section in each Table, it is taken that the evaluation criterion for the weight reduction rate is satisfied.

Evaluation of heat resistance: when the measurement result of the heat resistance of each cured product is equal to or more than the reference value shown for each experimental section in each Table, it is taken that the evaluation criterion for the heat resistance is satisfied.

Overall evaluation: when all of the above described three evaluation criteria are satisfied, the overall evaluation for the composition and the cured product therefrom is determined as "○".

TABLE I-10

| | | Example I 8-1 | Example I 8-2 | Comparative Example I 8-1 | Comparative Example I 8-2 | Comparative Example I 8-3 | Comparative Example I 8-4 |
|---|---|---|---|---|---|---|---|
| Composition (parts by mass) | Epoxy compound (I B-1) | 60 | 60 | 100 | 60 | 100 | 60 |
| | Monoepoxy compound (A) | 40 | 40 | | | | |
| | Reactive diluent (I C-2) | | | | 40 | | 40 |
| | Thermal cationic polymerization initiator (I E-3) | 2 | | 2 | 2 | | |
| | Thermal cationic polymerization initiator (I E-4) | | 2 | | | 2 | 2 |
| Viscosity of curable composition (mPa·s) | | 292 | 303 | 12150 | 21 | 11820 | 21 |
| Reference value for viscosity (mPa·s) | | 400 | 400 | 400 | 400 | 400 | 400 |
| Weight reduction rate of cured product (%) | | 1 | 13 | 0 | 14 | 7 | 22 |
| Reference value for weight reduction rate (%) | | 15 | 15 | 15 | 15 | 15 | 15 |
| Heat resistance of cured product (° C.) | | 124 | 110 | 158 | 100 | 230 | 94 |

TABLE I-10-continued

|  | Example I 8-1 | Example I 8-2 | Comparative Example I 8-1 | Comparative Example I 8-2 | Comparative Example I 8-3 | Comparative Example I 8-4 |
|---|---|---|---|---|---|---|
| Reference value for heat resistance (° C.) | 100 | 100 | 100 | 100 | 100 | 100 |
| Overall evaluation | ○ | ○ | x | x | x | x |

TABLE I-11

|  |  | Example I 8-3 | Example I 8-4 | Comparative Example I 8-5 | Comparative Example 18-6 | Comparative Example I 8-7 | Comparative Example I 8-8 |
|---|---|---|---|---|---|---|---|
| Composition (parts by mass) | Epoxy compound (I B-1) | 60 | 60 | 100 | 60 | 100 | 60 |
|  | Monoepoxy compound (A) | 40 | 40 |  |  |  |  |
|  | Reactive diluent (I C-2) |  |  |  | 40 |  | 40 |
|  | Thermal cationic polymerization initiator (I E-5) | 2 |  | 2 | 2 |  |  |
|  | Thermal cationic polymerization initiator (I E-6) |  | 2 |  |  | 2 | 2 |
| Viscosity of curable composition (mPa · s) |  | 294 | 293 | 12370 | 20 | 12150 | 21 |
| Reference value for viscosity (mPa · s) |  | 400 | 400 | 400 | 400 | 400 | 400 |
| Weight reduction rate of cured product (%) |  | 0 | 1 | 0 | 3 | 3 | 14 |
| Reference value for weight reduction rate (%) |  | 15 | 5 | 15 | 15 | 5 | 5 |
| Heat resistance of cured product (° C.) |  | 119 | 74 | 110 | 73 | 198 | 60 |
| Reference value for heat resistance (° C.) |  | 100 | 70 | 100 | 100 | 70 | 70 |
| Overall evaluation |  | ○ | ○ | x | x | x | x |

II. Examples of Aspect II of the Present Invention

II-1. Example II 1: Preparation of Curable Compositions Containing Monoepoxy Compound (A) and Evaluation Thereof (Part 1: Combination with Epoxy compound (II B-1) and Photo-cationic Polymerization Initiator (II D-1))

(1) Example II 1-1

Preparation of Curable Composition

The monoepoxy compound (A) obtained as described above, the other epoxy compound (II B-1), and a photo-cationic polymerization initiator (II D-1) were mixed to achieve the following composition, to prepare a curable composition.

<Composition of Curable Composition>

Monoepoxy compound (A)  25 parts by mass
(the monoepoxy compound produced by the method described in Example I 1-1)

The other epoxy compound (II B-1)  75 parts by mass
(a bisphenol A-type liquid epoxy resin, manufactured by Nippon Steel & Sunnikin Chemical Co., Ltd., trade name: YD-128)
Photo-cationic polymerization initiator (II D-1)  10 parts by mass
(a 50% propylene carbonate solution of an aromatic sulfoniunn salt: diphenyl-4-(phenylthio)phenylsulfoniunn hexafluorophosphate, manufactured by San-Apro Ltd., trade name: CPI-100P)

(2) Example II 1-2 and Example II 1-3

Curable compositions were obtained in the same manner as in Example II 1-1, except that the contents of the monoepoxy compound (A) and the other epoxy compound (II B-1) were changed to the amounts shown in Table II-1.

(3) Comparative Example II 1-1

A curable composition was prepared in the same manner as in Example II 1-1, except that 1,2-epoxy-4-vinylcyclohexane (manufactured by Daicel Corporation, trade name: CELLOXIDE 2000) was used instead of the monoepoxy compound (A).

(4) Comparative Example II 1-2 and Comparative Example II 1-3

Curable compositions were obtained in the same manner as in Comparative Example II 1-1, except that the contents of 1,2-epoxy-4-vinylcyclohexane and the other epoxy compound (II B-1) were changed to the amounts shown in Table II-1.

(5) Evaluation of Curable Compositions

<Adhesion Test (Measurement of Peeling Strength)>

Each of the curable compositions obtained in the above described Examples II 1-1 to II 1-3 and Comparative Examples II 1-1 to II 1-3 was coated on a PET film (manufactured by Toyobo Co., Ltd., trade name: COSMOS-HINE A4300) to a thickness of 5 μm, and the coated film was laminated with another piece of the same PET film. Subsequently, the resultant was irradiated with UV light at room temperature (23° C.) such that the accumulated amount of light was 1,500 mJ/cm² to cure the curable composition, thereby obtaining a laminated film for each of the compositions.

From each laminated film, a strip-shaped test specimen having a length of 150 mm and a width of 30 mm was cut out, and the peeling strength at 900 (at 23° C., and at a peeling speed of 300 mm/min) of each specimen was measured by Strograph E-L, manufactured by Toyo Seiki Co., Ltd. The measurement results are summarized in Table II-1. In the Table, a test specimen whose peeling strength was too high and thus resulted in the cohesive failure of the PET films was indicated as "Unable to measure". This indicates that the cured product from the composition in the test specimen has an adhesive force equal to or higher than the cohesive force of the PET films, and therefore means that it has an extremely excellent adhesive force.

<Composition of Curable Composition>

| | |
|---|---|
| Monoepoxy compound (A) | 50 parts by mass |
| (the monoepoxy compound produced by the method described in Example I 1-1) | |
| The other epoxy compound (II B-13) | 50 parts by mass |
| ((3,3',4,4'-diepoxy)bicyclohexyl, manufactured by Daicel Corporation, trade name: CELLOXIDE 8000) | |
| Photo-cationic polymerization initiator (II D-1) | 10 parts by mass |
| (a 50% propylene carbonate solution of an aromatic sulfonium salt: diphenyl-4-(phenylthio)phenylsulfonium hexafluorophosphate, manufactured by San-Apro Ltd., trade name: CPI-100P) | |

(2) Example II 2-2

A curable composition was prepared in the same manner as in Example II 2-1, except that the contents of the monoepoxy compound (A) and the other epoxy compound (II B-13) were changed to the amounts shown in Table II-2.

(3) Comparative Example II 2-1

A curable composition was prepared in the same manner as in Example II 2-1, except that 1,2-epoxy-4-vinylcyclohexane was used instead of the monoepoxy compound (A).

(4) Comparative Example II 2-2

A curable composition was obtained in the same manner as in Comparative Example II 2-1, except that the contents of 1,2-epoxy-4-vinylcyclohexane and the other epoxy compound (II B-13) were changed to the amounts shown in Table II-2.

TABLE II-1

| | | Example II 1-1 | Example II 1-2 | Example II 1-3 | Comparative Example II 1-1 | Comparative Example II 1-2 | Comparative Example II 1-3 |
|---|---|---|---|---|---|---|---|
| Composition of curable composition (parts by mass) | Epoxy compound (II B-1) | 75 | 50 | 25 | 75 | 50 | 25 |
| | Monoepoxy compound (A) | 25 | 50 | 75 | | | |
| | 1,2-Epoxy-4-vinylcyclohexane | | | | 25 | 50 | 75 |
| | Photo-cationic polymerization initiator (II D-1) | 10 | 10 | 10 | 10 | 10 | 10 |
| Peeling strength (N/m) | | 12 | 23 | Unable to measure | 1 | <1 | 5 |

II-2. Example II 2: Preparation of Curable Compositions Containing Monoepoxy Compound (A) and Evaluation Thereof (Part 2: Combination with Epoxy compound (II B-13) and Photo-cationic Polymerization initiator (II D-1))

(1) Example II 2-1

Preparation of Curable Composition

The monoepoxy compound (A) obtained as described above, the other epoxy compound (II B-13), and the photo-cationic polymerization initiator (II D-1) were mixed to achieve the following composition, to prepare a curable composition.

(5) Evaluation of Curable Compositions

<Adhesion Test (Measurement of Peeling Strength)>

Laminated films were obtained according to the method described in Example II 1 (5), using the curable compositions obtained in the above described Examples II 2-1 and II 2-2 as well as Comparative Examples II 2-1 and II 2-2, and the peeling strength of each of the specimens thereof was measured. The measurement results are summarized in Table II-2. In the Table, a test specimen whose peeling strength was too high and thus resulted in the cohesive failure of the PET films was indicated as "Unable to measure". This indicates that the cured product from the composition in the test specimen has an adhesive force equal to or higher than the cohesive force of the PET films, and therefore means that it has an extremely excellent adhesive force.

TABLE II-2

|  |  | Example II 2-1 | Example II 2-2 | Comparative Example II 2-1 | Comparative Example II 2-2 |
|---|---|---|---|---|---|
| Composition of curable composition (parts by mass) | Epoxy compound (II B-13) | 50 | 40 | 50 | 40 |
|  | Monoepoxy compound (A) | 50 | 60 |  |  |
|  | 1,2-Epoxy-4-vinylcyclohexane |  |  | 50 | 60 |
|  | Photo-cationic polymerization initiator (II D-1) | 10 | 10 | 10 | 10 |
| Peeling strength (N/m) |  | Unable to measure | Unable to measure | 7 | 5 |

II-3. Example II 3: Preparation of Curable Compositions Containing Monoepoxy Compound (A) and Evaluation Thereof (Part 3: Combination with Various Types of Epoxy Compounds and Photo-cationic Polymerization Initiator (II D-1) (1) Examples II 3-1 to II 3-8 and Comparative Examples II 3-1 to II 3-8

Curable compositions were obtained in the same manner as in Example II 1-1, except that the following components were used, at the compositions shown in Tables II-3 and II-4.

(i) Epoxy Compound (II B-2)

3',4'-Epoxycyclohexylmethyl 3,4-epoxycyclohexane carboxylate, manufactured by Daicel Corporation, trade name: CELLOXIDE 2021P, was used.

(ii) Epoxy Compound (II B-3)

A cresol novolac type epoxy resin, manufactured by DIC Corporation, trade name: N-660, was used.

(iii) Epoxy Compound (II B-5)

A bisphenol F-type liquid epoxy resin, manufactured by Nippon Steel & Sumikin Chemical Co., Ltd., trade name: YDF-170, was used.

(iv) Epoxy Compound (II B-6)

A hydrogenated bisphenol A-type liquid epoxy resin, manufactured by Mitsubishi Chemical Corporation, trade name: YX8000, was used.

(v) Epoxy Compound (II B-8)

Tetramethylene glycol diglycidyl ether, a reagent manufactured by Tokyo Chemical Industry Co., Ltd. was used.

(vi) Epoxy Compound (II B-9)

Cyclohexanedicarboxylic acid diglycidyl ester, a reagent manufactured by Tokyo Chemical Industry Co., Ltd. was used.

(vii) Epoxy Compound (II B-11)

1,2-Epoxy-(2-oxiranyl)cyclohexane adduct of 2,2-bis(hydroxymethyl)-1-butanol, manufactured by Daicel Corporation, trade name: EHPE 3150, was used.

(viii) Epoxy Compound (II B-14)

Tetrahydroindene diepoxide produced by the method described in JP 2012-116390 A was used.

(ix) Monoepoxy Compound (A)

The monoepoxy compound produced by the method described in Example I 1-1 was used.

(x) 1,2-Epoxy-4-vinylcyclohexane 1,2-Epoxy-4-vinylcyclohexane, manufactured by Daicel Corporation, trade name: CELLOXIDE 2000, was used.

(xi) Photo-cationic Polymerization Initiator (II D-1)

A 50% propylene carbonate solution of diphenyl-4-(phenylthio)phenylsulfonium hexafluorophosphate, manufactured by San-Apro Ltd., CPI-100P, was used.

(2) Evaluation of Curable Compositions

<Adhesion Test (Measurement of Peeling Strength)>

Laminated films were obtained according to the method described in Example II 1 (5), using the curable compositions obtained in the above described Examples II 3-1 to II 3-8 and Comparative Examples II 3-1 to II 3-8, and the peeling strength of each of the specimens thereof was measured. The measurement results are summarized in Tables II-3 and II-4. In the Tables, a test specimen whose peeling strength was too high and thus resulted in the cohesive failure of the PET films was indicated as "Unable to measure". This indicates that the cured product from the composition in the test specimen has an adhesive force equal to or higher than the cohesive force of the PET films, and therefore means that it has an extremely excellent adhesive force.

TABLE II-3

|  |  | Example II 3-1 | Example II 3-2 | Example II 3-3 | Example II 3-4 | Comparative Example II 3-1 | Comparative Example II 3-2 | Comparative Example II 3-3 | Comparative Example II 3-4 |
|---|---|---|---|---|---|---|---|---|---|
| Composition of curable composition (parts by mass) | Epoxy compound (II B-2) | 50 |  |  |  | 50 |  |  |  |
|  | Epoxy compound (II B-3) |  | 50 |  |  |  | 50 |  |  |
|  | Epoxy compound (II B-5) |  |  | 50 |  |  |  | 50 |  |
|  | Epoxy compound (II B-6) |  |  |  | 50 |  |  |  | 50 |
|  | Monoepoxy compound (A) | 50 | 50 | 50 | 50 |  |  |  |  |
|  | 1,2-Epoxy-4-vinylcyclohexane |  |  |  |  | 50 | 50 | 50 | 50 |
|  | Photo-cationic polymerization initiator (II D-1) | 10 | 10 | 10 | 10 | 10 | 10 | 10 | 10 |
| Peeling strength (N/m) |  | 20.8 | 12.6 | 21.9 | 10.9 | 3.5 | 5.4 | 2.9 | 2.8 |

TABLE II-4

|  |  | Example II 3-5 | Example II 3-6 | Example II 3-7 | Example II 3-8 | Comparative Example II 3-5 | Comparative Example II 3-6 | Comparative Example II 3-7 | Comparative Example II 3-8 |
|---|---|---|---|---|---|---|---|---|---|
| Composition of curable composition (parts by mass) | Epoxy compound (II B-8) | 50 |  |  |  | 50 |  |  |  |
|  | Epoxy compound (II B-9) |  | 50 |  |  |  | 50 |  |  |
|  | Epoxy compound (II B-11) |  |  | 50 |  |  |  | 50 |  |
|  | Epoxy compound (II B-14) |  |  |  | 50 |  |  |  | 50 |
|  | Monoepoxy compound (A) | 50 | 50 | 50 | 50 |  |  |  |  |
|  | 1,2-Epoxy-4-vinylcyclohexane |  |  |  |  | 50 | 50 | 50 | 50 |
|  | Photo-cationic polymerization initiator (II D-1) | 10 | 10 | 10 | 10 | 10 | 10 | 10 | 10 |
| Peeling strength (N/m) |  | 3.3 | 25.1 | Unable to measure | 10.5 | 3 | 3.1 | 12.7 | 2.9 |

II-4. Example II 4: Preparation of Curable Compositions Containing Monoepoxy Compound (A) and Evaluation Thereof (Part 4: Combination with Various Types of Oxetane Compounds and Photo-cationic Polymerization Initiator (II D-1))

(1) Examples II 4-1 and II 4-2, and Comparative Examples II 4-1 and II 4-2

Curable compositions were obtained in the same manner as in Example II 1-1, except that the following components were used, at the compositions shown in Table II-5.

(i) Monoepoxy Compound (A)

The monoepoxy compound produced by the method described in Example I 1-1 was used.

(ii) 1,2-Epoxy-4-vinylcyclohexane 1,2-Epoxy-4-vinylcyclohexane, manufactured by Daicel Corporation, trade name: CELLOXIDE 2000, was used.

(iii) Oxetane Compound (II C-2)

3-Ethyl-3-hydroxymethyloxetane, manufactured by Toagosei Co., Ltd., trade name: ARONE OXETANE OXT-101, was used.

(iv) Oxetane Compound (II C-3)

Di[(3-ethyl-3-oxetanyl)methyl]ether, manufactured by Toagosei Co., Ltd., trade name: ARONE OXETANE OXT-221, was used.

(v) Photo-cationic Polymerization Initiator (II D-1)

A 50% propylene carbonate solution of diphenyl-4-(phenylthio)phenylsulfonium hexafluorophosphate, manufactured by San-Apro Ltd., CPI-100P, was used.

(2) Evaluation of Curable Compositions

<Adhesion Test (Measurement of Peeling Strength)>

Laminated films were obtained according to the method described in Example II 1 (5), using the curable compositions obtained in the above described Examples II 4-1 and II 4-2 as well as Comparative Examples II 4-1 and II 4-2, and the peeling strength of each of the specimens thereof was measured. The measurement results are summarized in Table II-5.

TABLE II-5

|  |  | Example II 4-1 | Example II 4-2 | Comparative Example II 4-1 | Comparative Example II 4-2 |
|---|---|---|---|---|---|
| Composition of curable composition | Monoepoxy compound (A) | 50 | 50 |  |  |
|  | 1,2-Epoxy-4-vinylcyclohexane |  |  | 50 | 50 |
|  | Oxetane compound (II C-2) | 50 |  | 50 |  |

TABLE II-5-continued

|  |  | Example II 4-1 | Example II 4-2 | Comparative Example II 4-1 | Comparative Example II 4-2 |
|---|---|---|---|---|---|
| (parts by mass) | Oxetane compound (II C-3) |  | 50 |  | 50 |
|  | Photo-cationic polymerization initiator (II D-1) | 10 | 10 | 10 | 10 |
|  | Peeling strength (N/m) | 12.7 | 2.9 | 2.7 | 2.6 |

II-5. Example II 5: Preparation of Curable Compositions Containing Monoepoxy Compound (A) and Evaluation Thereof (Part 5: Combination with Epoxy Compound (II B-1) and Various Types of Photo-cationic Polymerization Initiators)

(1) Examples II 5-1 and II 5-2, and Comparative Examples II 5-1 and II 5-2

Curable compositions were obtained in the same manner as in Example II 1-1, except that the following components were used, at the compositions shown in Table II-6.

(i) Epoxy Compound (II B-1)

A bisphenol A-type liquid epoxy resin, manufactured by Nippon Steel & Sumikin Chemical Co., Ltd., trade name: YD-128, was used.

(ii) Monoepoxy Compound (A)

The monoepoxy compound produced by the method described in Example I 1-1 was used.

(iii) 1,2-Epoxy-4-vinylcyclohexane 1,2-Epoxy-4-vinylcyclohexane, manufactured by Daicel Corporation, trade name: CELLOXIDE 2000, was used.

(iv) Photo-cationic Polymerization Initiator (II D-2)

Diphenyl-4-(phenylthio)phenylsulfonium hexafluoroantimonate, manufactured by San-Apro Ltd., CPI-101A, was used.

(v) Photo-cationic Polymerization Initiator (II D-3)

Bis[4-(di(4-(2-hydroxyethoxy))phenylsulfonio)phenyl] sulfide bishexafluoroantimonate, manufactured by ADEKA CORPORATION, ADEKA ARKLS SP-170, was used.

(2) Evaluation of Curable Compositions

<Adhesion Test (Measurement of Peeling Strength)>

Laminated films were obtained according to the method described in Example II 1 (5), using the curable compositions obtained in the above described Examples II 5-1 and II 5-2 as well as Comparative Examples II 5-1 and II 5-2, and the peeling strength of each of the specimens thereof was measured. The measurement results are summarized in Table II-6. In the Table, a test specimen whose peeling strength was too high and thus resulted in the cohesive failure of the PET films was indicated as "Unable to measure". This indicates that the cured product from the composition in the test specimen has an adhesive force equal to or higher than the cohesive force of the PET films, and therefore means that it has an extremely excellent adhesive force.

TABLE II-6

|  |  | Example II 5-1 | Example II 5-2 | Comparative Example II 5-1 | Comparative Example II 5-2 |
|---|---|---|---|---|---|
| Composition of curable composition (parts by mass) | Epoxy compound (II B-1) | 50 | 50 | 50 | 50 |
|  | Monoepoxy compound (A) | 50 | 50 |  |  |
|  | 1,2-Epoxy-4-vinylcyclohexane |  |  | 50 | 50 |
|  | Photo-cationic polymerization initiator (II D-2) | 10 |  | 10 |  |
|  | Photo-cationic polymerization initiator (II D-3) |  | 10 |  | 10 |
|  | Peeling strength (N/m) | Unable to measure | 18.9 | 2.6 | 3.2 |

III. Examples of Aspect III of the Present Invention

III-1. Example III 1: Synthesis of Monoepoxy Compound (A-1)

Into a reaction vessel equipped with a thermometer, an agitator, a reflux tube and a dropping device, 3,132 g of a diolefin compound represented by the following Formula (3), 3,132 g of toluene and sodium acetate were charged. To the reactor, 3,783 g of a 38% aqueous solution of peracetic acid was added dropwise over five hours, while stirring at −5° C. While continuing to stir the mixture at −5° C., a reaction was allowed to proceed for 17 hours. Subsequently, a 10% aqueous solution of sodium sulfite was used to carry out a neutralization treatment, followed by a liquid separation operation. The resultant was then subjected to distillation at a pressure of 2 hPa and a bottom temperature of from 130 to 140° C., to obtain 2,109 g of a monoepoxy compound (A-1) satisfying the above described Formula (1), which is a colorless transparent liquid.

Figure 2:
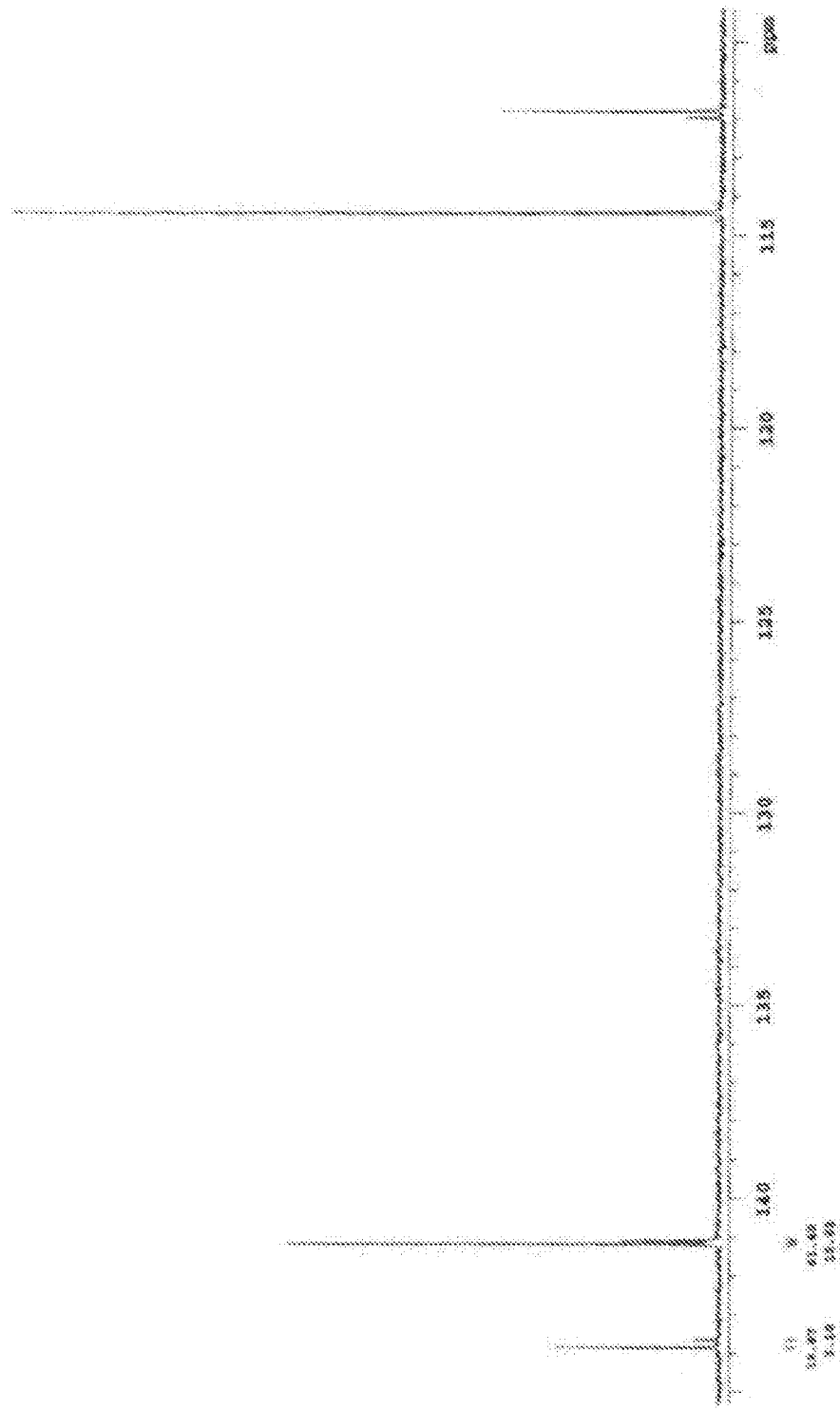
FIG. 2 shows a $^{13}$C-NMR chart of a monoepoxy compound (A-1) synthesized in Example III 1.

The $^{13}$C-NMR analysis of the thus obtained monoepoxy compound (A-1) was carried out under the following conditions. The ratio of peak areas derived from stereoisomers in which the bridgehead of the norbornane skeleton and the vinyl group are in a trans relationship, namely, peak areas derived from compounds represented by the following Formulae (4') and (5'), to the total peak area within the chemical shift range of from 140 to 145 ppm, was 77.03%. An NMR chart of the monoepoxy compound (A-1) is shown in FIG. 2.

NMR Analysis Conditions

Measurement apparatus: DD2 manufactured by Agilent Technologies Inc.
Probe: One
Measurement mode: complete decoupling
Cumulative number: 512
Repeating time: 2.13 s
Measurement time: 25 minutes
Solvent: deuterated chloroform
Temperature: 23° C.
Internal standard: deuterated chloroform According to the NMR chart shown in FIG. 2, the ratio of the total peak area within the chemical shift range of from 140 to 142 ppm to the total peak area within the chemical shift range of from 140 to 145 ppm, in the NMR analysis of the monoepoxy compound (A-1), was 77.03%. Further, according to the NMR chart shown in FIG. 2, the ratio of the area of the first peak from the low magnetic field side, within the chemical shift range of from 140 to 142 ppm, to the total peak area within the chemical shift range of from 140 to 145 ppm, in the NMR analysis of the monoepoxy compound (A-1), was 61.40%.

Figure 3:
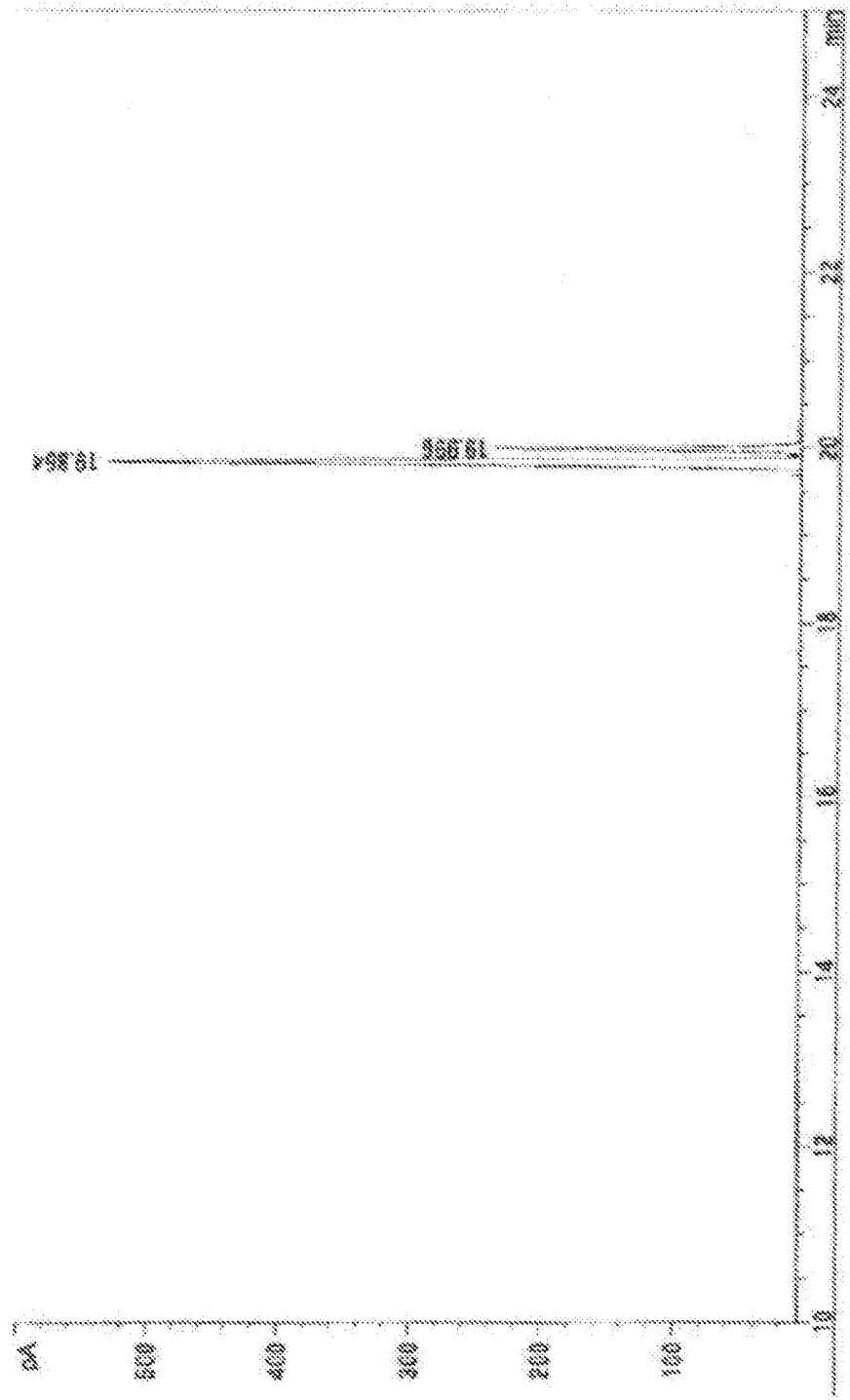
FIG. 3 shows a gas chromatograph of the monoepoxy compound (A-1) synthesized in Example III 1.

In addition, the gas chromatography analysis of the monoepoxy compound (A-1) was carried out under the following conditions. A gas chromatograph of the monoepoxy compound (A-1) is shown in FIG. 3.

Gas Chromatography Analysis Conditions

Measurement apparatus: Agilent 6850 series, manufactured by Agilent Technologies Inc.
Column: HP-1, dimethylpolysiloxane, length: 60.0 m, inner diameter: 250 μm, film thickness: 0.25 μm
Carrier gas: N$_2$
Flow velocity: 1.3 mL/min
Sample inlet temperature: 140° C.
Detector temperature: 250° C.
Sample injection volume: 0.2 μL
Temperature rise conditions: 80° C. (3 min), 80 to 150° C. (10° C./min), 150 to 250° C. (5° C./min), 250° C. (20 min)

[Chem. 19]

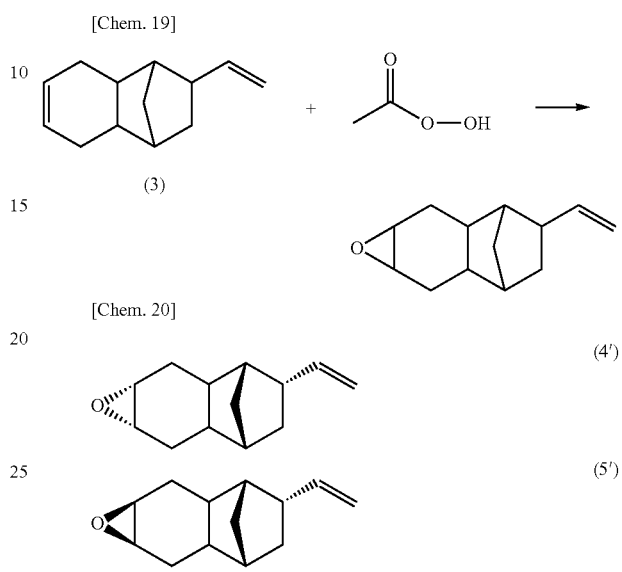

[Chem. 20]

III-2. Example III 2: Synthesis of Monoepoxy Compound (A-2)

Into a reaction vessel equipped with a thermometer, an agitator, a reflux tube and a dropping device, 6.4 g of 35% hydrogen peroxide and 0.36 g of H$_3$PW$_{12}$O$_{40}$ were charged, followed by stirring at 60° C. for 30 minutes. After cooling the resultant at 40° C., 80.11 g of the diolefin compound represented by the above described Formula (3), 0.13 g of cetylpyridinium chloride, and 596 g of chloroform were added thereto. Subsequently, 44.84 g of 35% hydrogen peroxide was added dropwise while stirring at 40° C., and a reaction was allowed to proceed at 40° C. for six hours. After the completion of the reaction, 450 g of chloroform was used to carry out a separation and extraction operation. The organic layer was washed with 300 mL of a 10% aqueous solution of sodium thiosulfate, 300 mL of a 10% aqueous solution of sodium carbonate, and 300 mL of pure water. After carrying out a dehydration operation with magnesium sulfate, a rotatory evaporator was used to remove the solvent contained therein by distillation. The resultant was then subjected to distillation at a pressure of 3 hPa and a bottom temperature of from 140 to 170° C., to obtain 4.9 g of a monoepoxy compound (A-2) of interest, at a bottom temperature of 167° C.

The $^{13}$C-NMR analysis of the thus obtained monoepoxy compound (A-2) was carried out under the above described conditions. The ratio of the peak areas derived from the stereoisomers in which the bridgehead of the norbornane skeleton and the vinyl group are in a trans relationship, to the total peak area within the chemical shift range of from 140 to 145 ppm, was 64.89%. An NMR chart of the monoepoxy compound (A-2) is shown in FIG. 4.

Figure 4:
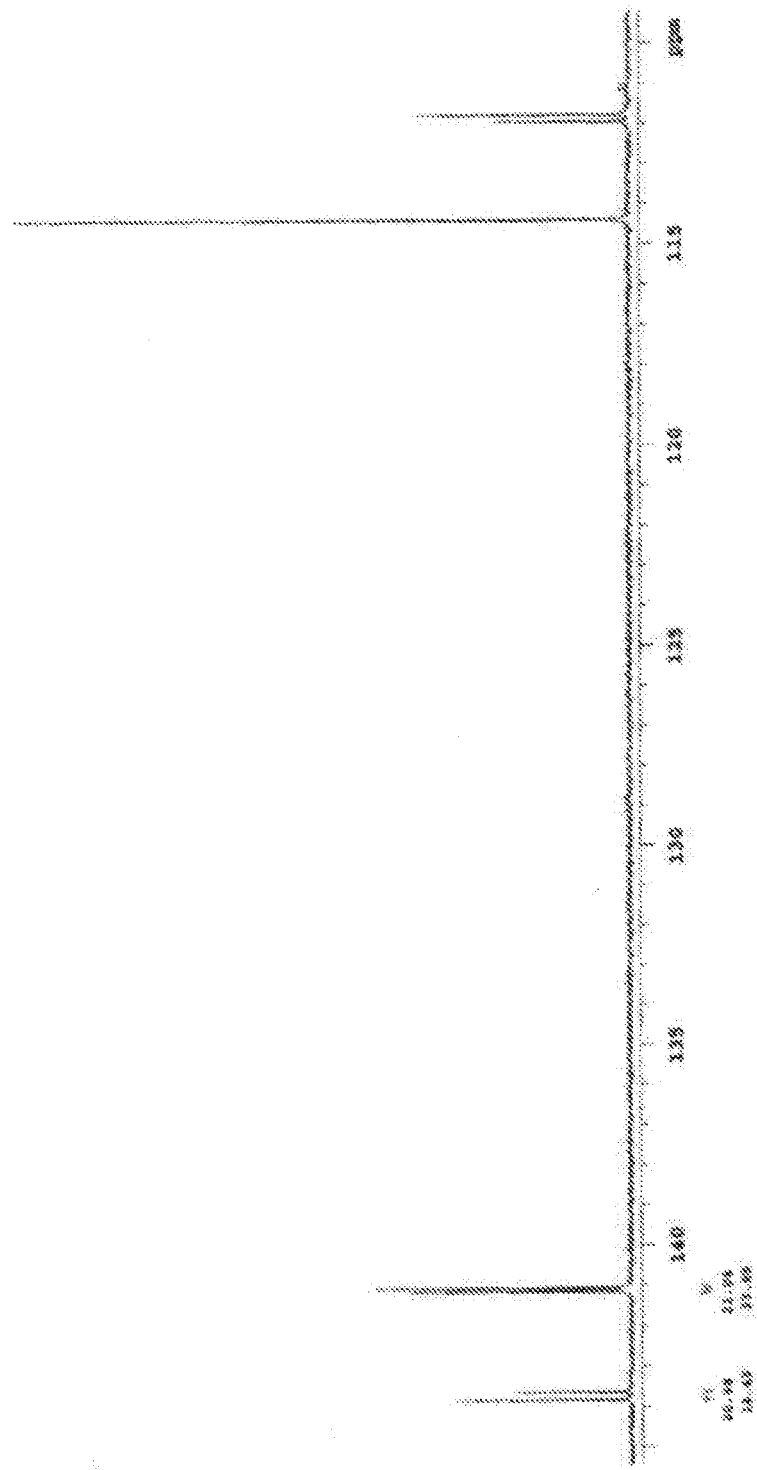
FIG. 4 shows a $^{13}$C-NMR chart of a monoepoxy compound (A-2) synthesized in Example III 2.

According to the NMR chart shown in FIG. 4, the ratio of the total peak area within the chemical shift range of from 140 to 142 ppm to the total peak area within the chemical shift range of from 140 to 145 ppm, in the NMR analysis of the monoepoxy compound (A-2), was 64.89%. Further, according to the NMR chart shown in FIG. 4, the ratio of the area of the first peak from the low magnetic field side, within the chemical shift range of from 140 to 142 ppm, to the total peak area within the chemical shift range of from 140 to 145 ppm, in the NMR analysis of the monoepoxy compound (A-2), was 31.04%.

Figure 5:
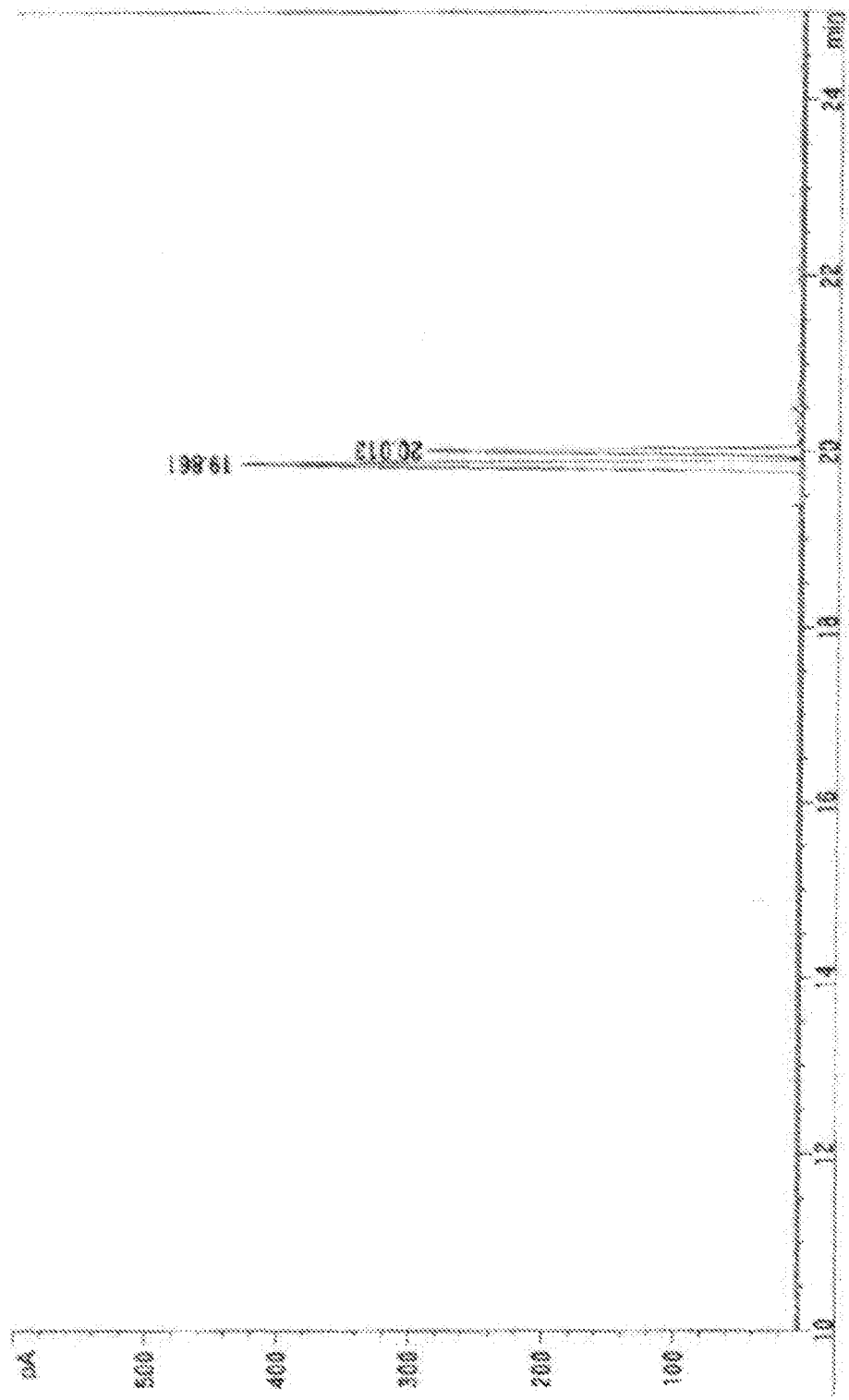
FIG. 5 shows a gas chromatograph of the monoepoxy compound (A-2) synthesized in Example III 2.

In addition, the gas chromatography analysis of the monoepoxy compound (A-2) was carried out, in the same manner as described above. A gas chromatograph of the monoepoxy compound (A-2) is shown in FIG. 5.

[Chem. 21]

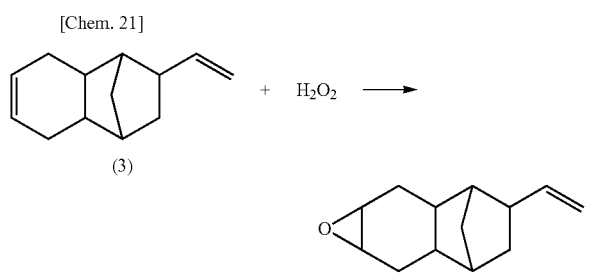

III-3. Example III 3: Preparation of Curable Compositions Containing Monoepoxy Compounds with Varying Stereoisomer Content and Thermal Cationic Polymerization Initiator, and Evaluation Thereof (Part 1)

Example III 3-1

The monoepoxy compound (A-1) obtained as described above, the other epoxy compound (III B-1), and a thermal cationic polymerization initiator were mixed to achieve the following composition, to prepare a curable composition.
<Composition of Curable Composition>

| | |
|---|---|
| Monoepoxy compound (A-1) | 60 parts by mass |
| The other epoxy compound (III B-1) | 40 parts by mass |
| (3',4'-epoxycyclohexylmethyl 3,4-epoxycyclohexane carboxylate, manufactured by Daicel Corporation, trade name: CELLOXIDE 2021P) | |
| Thermal cationic polymerization initiator | 1 part by mass |
| (aromatic sulfonium salt, manufactured by Sanshin Chemical Industry Co., Ltd., trade name: SI-80L) | |

Example III 3-2

A curable composition was obtained in the same manner as in Example III 3-1, except that the monoepoxy compound (A-2) was used instead of the monoepoxy compound (A-1).
<Evaluation of Heat Resistance>
The curable compositions obtained in the above described Examples and Comparative Examples were cured by heating in a hot air circulating oven at 60° C. for two hours, at 80° C. for two hours, at 120° C. for one hour, at 150° C. for one hour, and then at 180° C. for one hour, to obtain cured products.

The glass transition temperature of each of the thus obtained cured products was measured by increasing the temperature from 30 to 300° C. at a rate of 10° C./min, using a differential scanning calorimeter, DSC7020, manufactured by SII NanoTechnology Inc., and the thus measured value was taken as the heat resistance of the cured product. The glass transition temperature as used herein refers to a value measured in accordance with JIS K7121, based on "Midpoint Glass Transition Temperature: $T_{mg}$" described in the section of "Method for Measuring Transition Temperature of Plastics". The measurement results are summarized in Table III-1.

TABLE III-1

| | | Example III 3-1 | Example III 3-2 |
|---|---|---|---|
| Composition of curable resin composition (parts by mass) | Monoepoxy compound (A-1) | 60 | |
| | Monoepoxy compound (A-2) | | 60 |
| | Epoxy compound (III B-1) | 40 | 40 |
| | Thermal cationic polymerization initiator | 1 | 1 |
| Heat resistance of cured product (° C.) | | 145 | 135 |

III-4. Example III 4: Synthesis of Monoepoxy Compound (A-3)

During the distillation in the synthesis of the monoepoxy compound (A-2), 12.6 g of a fraction (A-3) was obtained at a bottom temperature of 151° C. The $^{13}$C-NMR analysis of the resulting monoepoxy compound (A-3) was carried out under the above described conditions. The ratio of the peak areas derived from the stereoisomers in which the bridgehead of the norbornane skeleton and the vinyl group are in a trans relationship, to the total peak area within the chemical shift range of from 140 to 145 ppm, was 72.32%. An NMR chart of the monoepoxy compound (A-3) is shown in FIG. 6.

Figure 6:
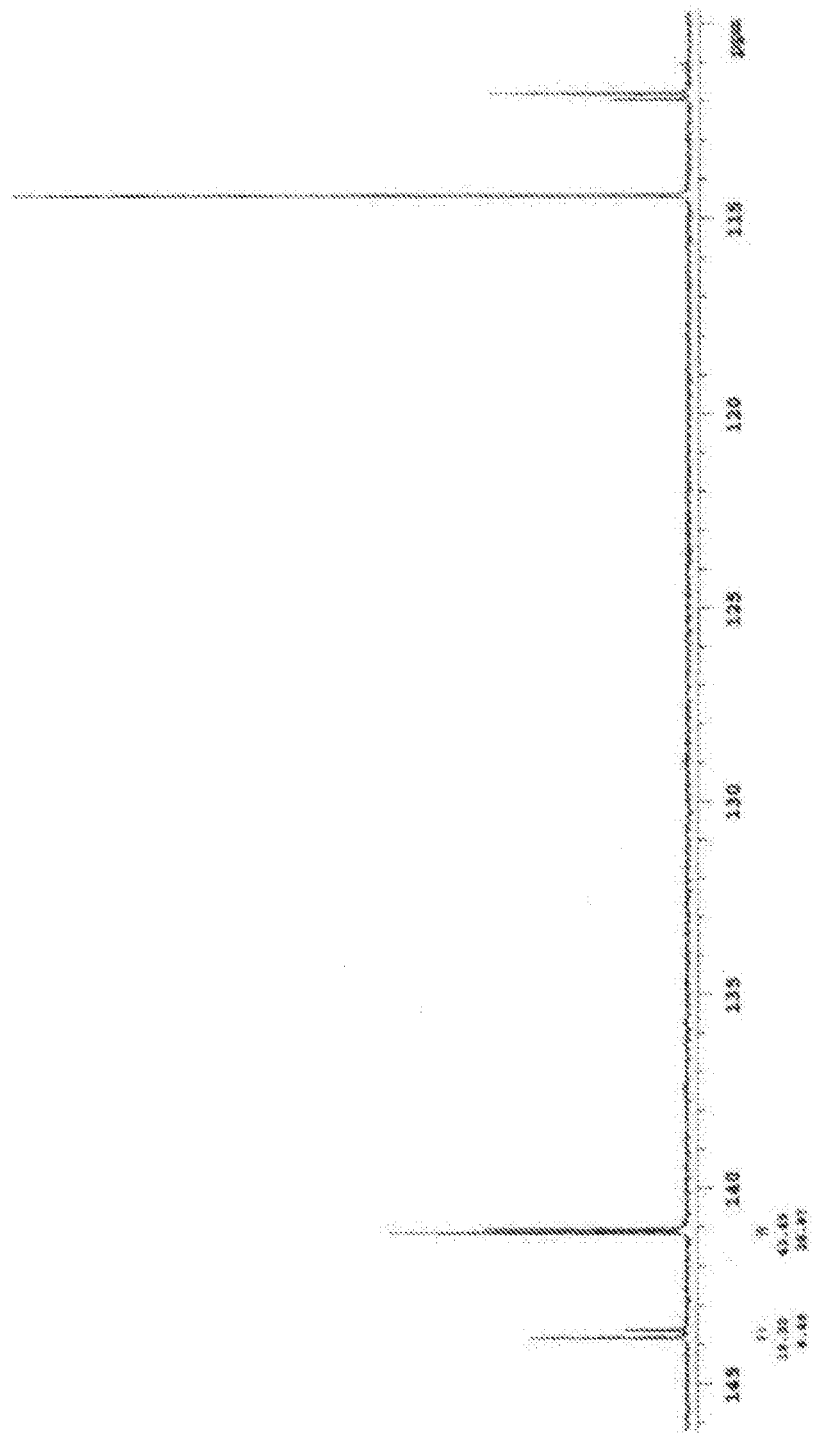
FIG. 6 shows a $^{13}$C-NMR chart of a monoepoxy compound (A-3) synthesized in Example III 4.

According to the NMR chart shown in FIG. 6, the ratio of the total peak area within the chemical shift range of from 140 to 142 ppm to the total peak area within the chemical shift range of from 140 to 145 ppm, in the NMR analysis of the monoepoxy compound (A-3), was 72.32%. Further, according to the NMR chart shown in FIG. 6, the ratio of the area of the first peak from the low magnetic field side, within the chemical shift range of from 140 to 142 ppm, to the total peak area within the chemical shift range of from 140 to 145 ppm, in the NMR analysis of the monoepoxy compound (A-3), was 43.45%.

Figure 7:
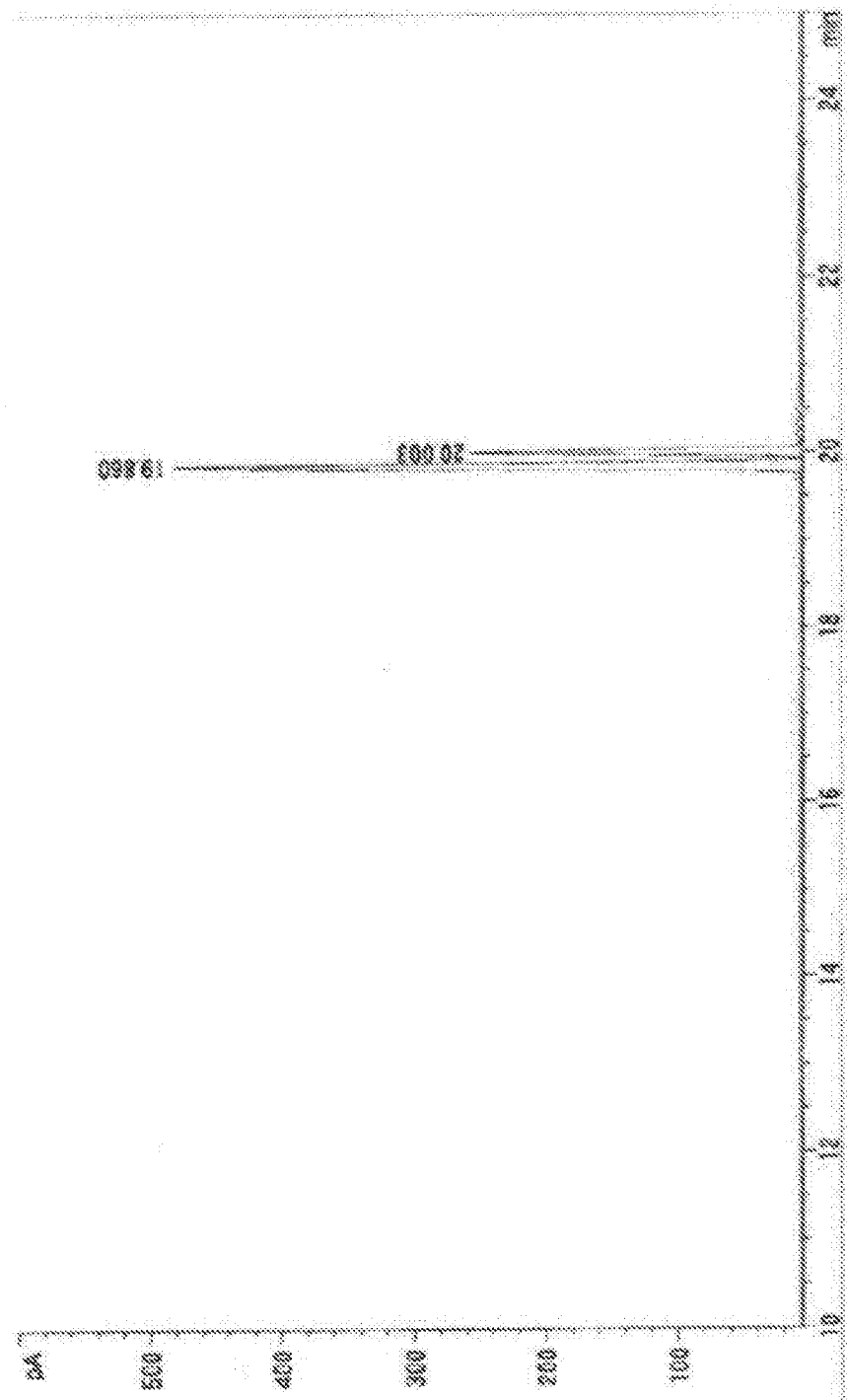
FIG. 7 shows a gas chromatograph of the monoepoxy compound (A-3) synthesized in Example III 4.

In addition, the gas chromatography analysis of the monoepoxy compound (A-3) was carried out, in the same manner as described above. A gas chromatograph of the monoepoxy compound (A-3) is shown in FIG. 7.

III-5. Example III 5: Preparation of Curable Compositions Containing Monoepoxy Compounds with Varying Stereoisomer Content and Thermal Cationic Polymerization Initiator, and Evaluation Thereof (Part 2: Combination with the Other Epoxy Compound)

Example III 5-1

The monoepoxy compound (A-1) obtained as described above, the other epoxy compound (III B-2), and a thermal cationic polymerization initiator were mixed to achieve the following composition, to prepare a curable composition.

<Composition of Curable Composition>

| | |
|---|---|
| Monoepoxy compound (A-1) | 40 parts by mass |
| The other epoxy compound (III B-2) (a bisphenol A-type liquid epoxy resin, manufactured by Nippon Steel & Sunnikin Chemical Co., Ltd., trade name: YD-128) | 60 parts by mass |
| Thermal cationic polymerization initiator (aromatic sulfoniunm salt, manufactured by Sanshin Chemical Industry Co., Ltd., trade name: SI-80L) | 1 part by mass |

Example III 5-2

A curable composition was obtained in the same manner as in Example III 5-1, except that the monoepoxy compound (A-3) synthesized as described below was used instead of the monoepoxy compound (A-1).

Example III 5-3

A curable composition was obtained in the same manner as in Example III 5-1, except that the monoepoxy compound (A-2) was used instead of the monoepoxy compound (A-1).
<Evaluation of Heat Resistance>

The curable compositions obtained in the above described Examples and Comparative Examples were cured by heating in a hot air circulating oven at 80° C. for one hour, at 120° C. for two hours, and then at 180° C. for two hours, to obtain cured products. The glass transition temperature of each of the thus obtained cured products was measured in the same manner as in Example III 3-1. The measurement results are summarized in Table III-2.

TABLE III-2

| | | Example III 5-1 | Example III 5-2 | Example III 5-3 |
|---|---|---|---|---|
| Composition of curable resin composition (parts by mass) | Monoepoxy compound (A-1) | 40 | | |
| | Monoepoxy compound (A-3) | | 40 | |
| | Monoepoxy compound (A-2) | | | 40 |
| | Epoxy compound (III B-2) | 60 | 60 | 60 |
| | Thermal cationic polymerization initiator | 1 | 1 | 1 |
| Heat resistance of cured product (° C.) | | 137 | 136 | 133 |

III-6. Example III 6: Preparation of Curable Compositions Containing Monoepoxy Compounds with Varying Stereoisomer Content and Acid Anhydride-based Curing Agent, and Evaluation Thereof (Part 1)

Example III 6-1

The monoepoxy compound (A-1) obtained as described above, the other epoxy compound (III B-1), an acid anhydride-based curing agent, and a curing accelerator were mixed to achieve the following composition, to prepare a curable composition.
<Composition of Curable Composition>

| | |
|---|---|
| Monoepoxy compound (A-1) | 50 parts by mass |
| The other epoxy compound (III B-1) | 100 parts by mass |
| Acid anhydride-based curing agent | 155 parts by mass |

-continued

| | |
|---|---|
| (a mixture of 4-methylhexahydrophthalic anhydride and hexahydrophthalic anhydride, manufactured by New Japan Chemical Co., Ltd., trade name: MH-700; an amount corresponding to 0.9 equivalent with respect to one equivalent of the monoepoxy compound (A-1) and the other epoxy compound (III B-1)) | |
| Curing accelerator (2-ethyl-4-methylimidazole, manufactured by Shikoku Chemicals Corporation, trade name: 2E4MZ) | 3 parts by mass |

Example 6-2

A curable composition was obtained in the same manner as in Example (III 6-1), except that the monoepoxy compound (A-2) was used instead of the monoepoxy compound (A-1).
<Evaluation of Heat Resistance>

The curable compositions obtained in the above described Examples and Comparative Examples were cured by heating in a hot air circulating oven at 100° C. for two hours, at 160° C. for two hours, and then at 220° C. for two hours, to obtain cured products.

The glass transition temperature of each of the thus obtained cured products was measured in the same manner as in Example III 3-1. The measurement results are summarized in Table III-3.

TABLE III-3

| | | Example III 6-1 | Example III 6-2 |
|---|---|---|---|
| Composition of curable resin composition (parts by mass) | Monoepoxy compound (A-1) | 50 | |
| | Monoepoxy compound (A-2) | | 50 |
| | Epoxy compound (III B-1) | 100 | 100 |
| | Curing agent | 155 | 155 |
| | Curing accelerator | 3 | 3 |
| Heat resistance of cured product (° C.) | | 168 | 157 |

III-7. Example III 7: Preparation of Curable Compositions Containing Monoepoxy Compounds with Varying Stereoisomer Content and Acid Anhydride-based Curing Agent, and Evaluation Thereof (Part 2: Combination with the Other Epoxy Compound)

Example III 7-1

The monoepoxy compound (A-1) obtained as described above, the other epoxy compound (III B-2), the acid anhydride-based curing agent, and the curing accelerator were mixed to achieve the following composition, to prepare a curable composition.
<Composition of Curable Composition>

| | |
|---|---|
| Monoepoxy compound (A-1) | 55.5 parts by mass |
| The other epoxy compound (III B-2) | 100 parts by mass |
| Acid anhydride-based curing agent | 125 parts by mass |
| Curing accelerator | 3 parts by mass |

Example III 7-2

A curable composition was obtained in the same manner as in Example III 7-1, except that the monoepoxy compound (A-2) was used instead of the monoepoxy compound (A-1).
<Evaluation of Heat Resistance>

The curable compositions obtained in the above described Examples and Comparative Examples were cured by heating in a hot air circulating oven at 100° C. for two hours, and then at 160° C. for four hours, to obtain cured products.

The glass transition temperature of each of the thus obtained cured products was measured in the same manner as in Example III 3-1. The measurement results are summarized in Table III-4.

TABLE III-4

| | | Example III 7-1 | Example III 7-2 |
|---|---|---|---|
| Composition of curable resin composition (parts by mass) | Monoepoxy compound (A-1) | 55.5 | |
| | Monoepoxy compound (A-2) | | 55.5 |
| | Epoxy compound (III B-2) | 100 | 100 |
| | Curing agent | 125 | 125 |
| | Curing accelerator | 3 | 3 |
| Heat resistance of cured product (° C.) | | 126 | 117 |

The invention claimed is:

1. A monoepoxy compound represented by the following Formula (1):

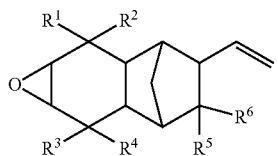

(1)

wherein $R^1$ to $R^6$ are each independently selected from the group consisting of a hydrogen atom, an alkyl group having from 1 to 10 carbon atoms, and an alkoxy group having from 1 to 10 carbon atoms.

2. The monoepoxy compound according to claim 1, comprising a stereoisomer(s) of the compound represented by the Formula (1), wherein the ratio, as measured by $^{13}$C-NMR analysis, of a peak area(s) derived from a stereoisomer(s) in which the bridgehead of the norbornane skeleton and the vinyl group in the Formula (1) are in a trans relationship, to the total peak area within the chemical shift range of from 140 to 145 ppm, is 66% or more.

3. The monoepoxy compound according to claim 2, wherein $R^1$ to $R^6$ are all hydrogen atoms, and the stereoisomer(s) in which the bridgehead of the norbornane skeleton and the vinyl group are in a trans relationship is/are represented by any of the following Formulae:

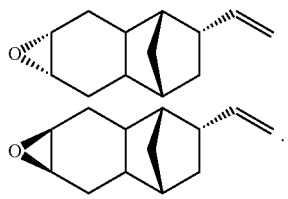

4. The monoepoxy compound according to claim 1, wherein, in the $^{13}$C-NMR analysis of the compound represented by the Formula (1), the ratio of the total peak area within the chemical shift range of from 140 to 142 ppm to the total peak area within the chemical shift range of from 140 to 145 ppm is 66% or more.

5. The monoepoxy compound according to claim 2, wherein, in the $^{13}$C-NMR analysis of the compound represented by the Formula (1), the ratio of the area of the first peak from the low magnetic field side, among peaks within the chemical shift range of from 140 to 142 ppm, to the total peak area within the chemical shift range of from 140 to 145 ppm is 35% or more.

6. A curable composition comprising:
the monoepoxy compound according to claim 1; and
one kind selected from the group consisting of a curing agent, a thermal cationic polymerization initiator, and a photo-cationic polymerization initiator.

7. The curable composition according to claim 6, wherein the curing agent is one or more curing agents selected from the group consisting of phenol compounds, amine compounds, acid anhydride-based compounds, and an amide compounds.

8. The curable composition according to claim 6, wherein the thermal cationic polymerization initiator is selected from the group consisting of aromatic sulfonium salt-based thermal cationic polymerization initiators, aromatic iodonium salt-based thermal cationic polymerization initiators, and aluminum complex-based thermal cationic polymerization initiators.

9. The curable composition according to claim 6, wherein the photo-cationic polymerization initiator is an aromatic sulfonium salt-based photo-cationic polymerization initiator.

10. The curable composition according to claim 6, further comprising another epoxy compound different from the monoepoxy compound represented by the Formula (1).

11. The curable composition according to claim 10, wherein the other epoxy compound different from the monoepoxy compound represented by the Formula (1) is selected from the group consisting of glycidyl ether-type epoxides, glycidyl ester-type epoxides, alicyclic epoxides, and epoxy resins.

12. The curable composition according to claim 10, wherein the content ratio of the monoepoxy compound to the other epoxy compound different from the monoepoxy compound represented by the Formula (1), in the curable composition, is from 1:99 to 75:25 on a mass basis.

13. A method of producing a cured product, the method comprising the step of curing the curable composition according to claim 6.

14. A cured product from the curable composition according to claim 6.

15. A method of producing the monoepoxy compound according to claim 1, the method comprising the step of allowing a compound represented by the following Formula (2):

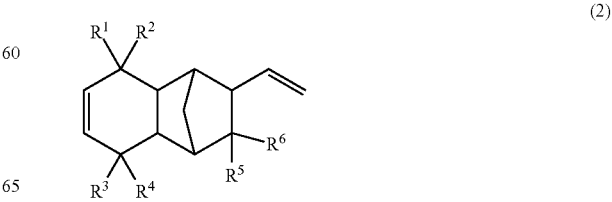

(2)

wherein $R^1$ to $R^6$ are each independently selected from the group consisting of a hydrogen atom, an alkyl group having from 1 to 10 carbon atoms, and an alkoxy group having from 1 to 10 carbon atoms to react with a peracid,
   wherein the peracid is used in an amount of from 0.10 to 1.80 mol, with respect to 1.00 mol of the compound represented by the Formula (2).

16. The method according to claim 15, wherein the peracid is hydrogen peroxide or an organic peracid.

17. A reactive diluent comprising at least the monoepoxy compound according to claim 1.

* * * * *